(12) United States Patent
O'Brien et al.

(10) Patent No.: US 9,950,016 B2
(45) Date of Patent: Apr. 24, 2018

(54) CELL SECRETED PROTEINS FOR THE TREATMENT OF MYOCARDIAL INFARCTION

(75) Inventors: Timothy O'Brien, Bushypark (IE); Frank Barry, Oughterard (IE); Claire Kavanagh, Naas (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 0 days.

(21) Appl. No.: 14/127,991

(22) PCT Filed: Jun. 25, 2012

(86) PCT No.: PCT/EP2012/062261
§ 371 (c)(1),
(2), (4) Date: May 12, 2014

(87) PCT Pub. No.: WO2012/175745
PCT Pub. Date: Dec. 27, 2012

(65) Prior Publication Data
US 2014/0242142 A1 Aug. 28, 2014

Related U.S. Application Data

(60) Provisional application No. 61/501,072, filed on Jun. 24, 2011.

(51) Int. Cl.
| | |
|---|---|
| *A01N 63/00* | (2006.01) |
| *A61K 35/545* | (2015.01) |
| *A61K 38/19* | (2006.01) |
| *A61K 38/17* | (2006.01) |
| *A61K 38/18* | (2006.01) |
| *A61K 38/39* | (2006.01) |
| *A61K 35/28* | (2015.01) |
| *A61K 35/44* | (2015.01) |
| *A61K 38/21* | (2006.01) |
| *A61K 38/36* | (2006.01) |
| *A61L 15/44* | (2006.01) |
| *A61L 27/28* | (2006.01) |
| *A61L 27/38* | (2006.01) |
| *A61L 27/54* | (2006.01) |
| *A61L 29/08* | (2006.01) |
| *A61L 29/16* | (2006.01) |

(52) U.S. Cl.
CPC .......... *A61K 35/545* (2013.01); *A61K 35/28* (2013.01); *A61K 35/44* (2013.01); *A61K 38/177* (2013.01); *A61K 38/1709* (2013.01); *A61K 38/179* (2013.01); *A61K 38/1735* (2013.01); *A61K 38/1891* (2013.01); *A61K 38/19* (2013.01); *A61K 38/195* (2013.01); *A61K 38/217* (2013.01); *A61K 38/363* (2013.01); *A61K 38/39* (2013.01); *A61L 15/44* (2013.01); *A61L 27/28* (2013.01); *A61L 27/3804* (2013.01); *A61L 27/54* (2013.01); *A61L 29/08* (2013.01); *A61L 29/16* (2013.01)

(58) Field of Classification Search
CPC .............. A61K 38/1735; A61K 38/217; A61K 38/195; A61K 38/1709; A61K 38/39; A61K 35/28; A61K 35/44; A61K 35/545; A61K 38/177; A61K 38/179; A61K 38/1891; A61K 38/19; A61K 38/363; A61L 27/28; A61L 15/44; A61L 27/54; A61L 27/3804; A61L 29/08; A61L 29/16
USPC ...................................................... 424/93.21
See application file for complete search history.

(56) References Cited

U.S. PATENT DOCUMENTS

2011/0262393 A1* 10/2011 Yang et al. .................. 424/85.2

FOREIGN PATENT DOCUMENTS

| EP | 2226079 | 8/2006 |
| WO | WO 2008/130588 A1 * | 10/2008 |
| WO | 2010056075 | 5/2010 |
| WO | 2012175745 | 12/2012 |

OTHER PUBLICATIONS

Maxeiner et al., 2010, Eu. J. Heart failure 12:730-737.*
Brekken et al 2004, J. Histochem. Cytochem. 52:735-748.*
Baker et al 2005, Am, J. Pathol. 166:923-933.*
Grisafi et al (2008, Stem Cells and Development . 17:953-962.*
Wagner et al 2005, Experimental Hematol. 33:1402-1416.*
Bosch et al 2006, Mol. Reprod. Dev. 73:1393-1403.*
Asahara, et al., (1999) "Bone marrow origin of endothelial progenitor cellsresponsible for postnatal vasculogenesis in physiological and pathological neovascularization", Circ Res, 85, 221-228. (9 pages total).
Barker, et al., (2005) "Matricellular homologs in the foreign body response: hevin suppresses inflammation, but hevin and SPARC together diminish angiogenesis", Am J Pathol, 166, 923-933 (11 pages total).
Beltrami, et al., (2001) "Evidence that human cardiac myocytes divide after myocardial infarction", N Engl J Med, 344, 1750-1757 (8 pages total).
Caplan, AI. & Dennis, I.E., (2006) "Mesenchymal stem cells as trophic mediators", J Cell Biochem, 98, 1076-1084 (9 pages total).
Gnecchi, et al., (2006) Evidence supporting paracrine hypothesis for Akt-modified mesenchymal stem cell-mediated cardiac protection and functional improvement, Faseb J, 20, 661-669 (9 pages total).
Kamihata, et al., (2001) "Implantation of bone marrow mononuclear cells into ischemic myocardium enhances collateral perfusion and regional function via side supply of angioblasts, angiogenic ligands, and cytokines", Circulation, 104, 1046-1052 (8 pages total).

(Continued)

*Primary Examiner* — Christopher M Babic
*Assistant Examiner* — Kelaginamane Hiriyanna
(74) *Attorney, Agent, or Firm* — Leason Ellis LLP

(57) ABSTRACT

The present invention relates to the use of secreted proteins from mesenchymal stem cells and other cells for the treatment of myocardial infarction. In particular, the invention provides compositions and methods based on secreted proteins from mesenchymal stem cells and the genes encoding them.

7 Claims, 10 Drawing Sheets

(56) References Cited

OTHER PUBLICATIONS

Kinnaird, et al., (2004) "Local delivery of marrow-derived stromal cells augments collateral perfusion through paracrine mechanisms", Circulation, 109, 1543-1549 (9 pages total).

Le Jan, et al., (2003) "Angiopoietin-like 4 is a proangiogenic factor produced during ischemia and in conventional renal cell carcinoma", Am J Pathol, 162, 1521-1528 (8 pages total).

McCurdy, et al., (2009) "Cardiac extracellular matrix remodeling: Fibrillar collagens and Secreted Protein Acidic and Rich in Cysteine (SPARC)", J Mol Cell Cardiol. (12 pages total).

Mirotsou, et al., (2007) "Secreted frizzled related protein 2 (Sfrp2) is the key Akt-mesenchymal stem cell-released paracrine factor mediating myocardial survival and repair", Proc Natl Acad Sci USA, 104, 1643-1648 (6 pages total).

Schellings, et al., (2009) "Absence of SP ARC results in increased cardiac rupture and dysfunction after acute myocardial infarction", J Exp Med, 206, 113-123 (11 pages total).

Simpson, et al., (1982) "Myocyte hypertrophy in neonatal rat heart cultures and its regulation by serum and by catecholamines" Circ Res, 51, 787-801 (16 pages total).

Slevin, et al., (2009) "Identification of pro-angiogenic markers in blood vessels from stroked-affected brain tissue using laser-capture microdissection", BMC Genomics, 10, 113 (15 pages total).

Song, et al., (2005) "Transfection of mesenchymal stem cells with the FGF-2 gene improves their survival under hypoxic conditions", Mol Cells, 19, 402-407 (6 pages total).

Strauer, et al., (2002) "Repair of infarcted myocardium by autologous intracoronary mononuclear bone marrow cell transplantation in humans", Circulation, 106, 1913-1918 (7 pages total).

Tang, et al., (2005) "Paracrine action enhances the effects of autologous mesenchymal stem cell transplantation on vascular regeneration in rat model of myocardial infarction", Ann Thorac Surg, 80, 229-236; discussion 236-227 (9 pages total).

Tressel, et al., (2008) "Angiopoietin-2 stimulates blood flow recovery after femoral artery occlusion by inducing inflammation and arteriogenesis", Arterioscler Thromb Vase Biol, 28, 1989-1995 (15 pages total).

Wollert, K.C. & Drexler, H. (2005) "Clinical applications of stem cells for the heart", Circ Res, 96, 151-163 (14 pages total).

Dobson, et al.. (1999) "Centrifugal isolation of bone marrow from bone: an improved method for the recovery and quantitation of bone marrow osteoprogenitor cells from rat tibiae and femurae", Calcif Tissue Int. 65(5): 411-3.

Halkos, et al. (2008) "Intravenous infusion of mesenchymal stem cells enhances regional perfusion and improves ventricular function in a porcine model of myocardial infarction", Basic Res Cardiol, 103, 525-536.

Katritsis, et al., (2005) Transcoronary transplantation of autologous mesenchymal stem cells and endothelial progenitors into infarcted human myocardium, Catheter Cardiovasc Interv, 65, 321-329.

Lau, et al., (2006) "SPARC and Hevin expression correlate with tumour angiogenesis in hepatocellular carcinoma", J Pathol, 210, 459-468.

Li, et al., (2007) "Bcl-2 engineered MSCs inhibited apoptosis and improved heart function", Stem Cells, 25, 2118-2127.

Liu, et al.. (2002) "An experimental study of anti-angiogenesis with recombinant human kringle 5", Zhonghua Yan Ke Za Zhi, 38,415-418.

Revised International Search Report issued in corresponding International Application No. PCT/EP2012/062261 dated Nov. 29, 2012.

Written Opinion issued in corresponding International Application No. PCT/EP2012/062261 dated Nov. 29, 2012.

Schellings Mark W M et al: "Absence of SPARC results in increased cardiac rupture and dysfunction after acute myocardial infarction", Journal of Experimental Medicine, vol. 206, No. I, Jan. 16, 2009.

Lively S et al: Expression of the extracellular matrix molecule, SCI/hevin, after a hemorrhagic stroke & Society for Neuroscience Abstract Viewer, and Itinerary Planner, vol. 40, 2010, 40th Annual Meeting of the Society-For-Neuroscience; San Diego, CA, USA; Nov. 13-17, 2010.

\* cited by examiner

CELL SECRETED PROTEINS FOR THE TREATMENT OF MYOCARDIAL INFARCTION

CROSS-REFERENCE TO RELATED APPLICATIONS

This application is a national stage under 35 U.S.C. 371 based on and claiming the benefit of International Application PCT/EP2012/062261, filed on Jun. 25, 2012, incorporated by reference, which claims the benefit of priority from U.S. Provisional Application No. 61/501,072, filed on Jun. 24, 2011, the entire contents of each of which are incorporated herein by reference.

FIELD OF THE INVENTION

The present invention relates to the use of secreted proteins from mesenchymal stem cells and other cells for the treatment of myocardial infarction. In particular, the invention provides compositions and methods based on secreted proteins from mesenchymal stem cells and the genes encoding them.

BACKGROUND TO THE INVENTION

The molecular and cellular mechanisms mediating heart failure including cardiac myocyte apoptosis and necrosis, cardiac myocyte hypertrophy, interstitial fibrosis, decreased contractility, inflammation, oxidative stress and impaired neovascularisation have been the focus of numerous research efforts (Wollert and Drexler 2005). Cell based cardiac therapy aims to correct the root cause of heart failure symptoms, namely the inability of the injured heart to adequately pump blood due to insufficient muscle mass. Cellular cardiomyoplasty is increasingly recognised as having the potential to salvage damaged myocardium and to promote endogenous repair of cardiac tissue by replacement of damaged cardiomyocytes and promotion of neovascularisation. The functional benefits observed following mesenchymal stem cell (MSC) delivery after myocardial infarction (MI) have been attributed by some to transdifferentiation or cellular fusion causing cardiomyocyte regeneration or vasculogenesis (Halkos, et al 2008).

Other studies suggest the beneficial effects of MSCs are through indirect mechanisms promoting angiogenesis and neovascularisation (Asahara, et al 1999) or through the release of therapeutic soluble factors (Mirotsou, et al 2007). Confirmation of this paracrine hypothesis was demonstrated when a functional improvement was reported within 72 hours of MSC transplantation into the damaged myocardium. This short 72 hour time period suggested that the improved functional outcome could not be attributable to myocardial regeneration by the donor cells alone but by the release of soluble factors by these cells acting in a paracrine nature to limit infarct size and improve left ventricular function (Gnecchi, et al 2006).

Despite the overwhelming number of research groups working in the cardiovascular field, there are many key physiological questions that still remain unanswered. Of particular importance is better understanding of the fate and function of the MSCs following their delivery to the injured myocardium. It is unknown whether the MSCs persist in the myocardium or differentiate to cardiomyocytes or to other mesenchymal lineages in the myocardium. It is also unknown whether the MSCs contribute to neovascularisation or what, if any, soluble factors are being produced by these 'cell factories' that may be therapeutically relevant in the setting of MI.

This study aims to address some of these outstanding questions relating to the stem cell-host interaction in the context of the ischemic heart. This approach involved the direct retrieval of engrafted MSCs from the infarcted myocardium using two separate isolation techniques Laser Microdissection (LMD) and Fluorescent Activated Cell Sorting (FACS). Retrieval of engrafted MSCs from the infarcted myocardium allowed changes in the phenotype and genotype of the engrafted MSCs to be explored by comparing these characteristics to those of untransplanted control MSCs. Dissecting the mechanistic basis of cardioprotection, regeneration and differentiation following stem cell engraftment will help us further elucidate the therapeutic role of these cells in cardiac repair and identify key factors crucial to the repair process following MI. This work represents an important advancement in stem cell therapy. Harnessing the therapeutic potential of proteins produced by MSCs may overcome the issues of cell viability and scalability currently limiting the widespread clinical development of cellular cardiomyoplasty by delivery of the therapeutic protein itself. Identifying MSCs as potential cell factories responsible for the production of soluble factors to promote angiogenesis, cardiomyocyte regeneration and protection is a major step forward in cardiac repair. Furthermore, it provides a potential strategy for delivering specific therapeutic proteins produced by the cells rather than the cells themselves.

OBJECT OF THE INVENTION

It is an object of the present invention to elucidate the mechanisms and identify the factors involved in cardioprotection, regeneration and differentiation following stem cell engraftment in cardiac repair. A further objective is to provide compositions and methods comprising such factors for use in the treatment of vascular diseases and associated vascular complications.

SUMMARY OF THE INVENTION

According to the present invention there is provided a pharmaceutical composition comprising one or more proteins secretable by mesenchymal stem cells and a pharmaceutically acceptable carrier or excipient. The protein may be selected from the group comprising Sparcl1, Sfrp2, Fgl2, TEK, Angptl4, Notch1, Podxl, Lama2, Cthrc1, Cxcl 10, Il 1α, Ifn g, or combinations thereof. The proteins may be secreted by mesenchymal stem cells or by endothelial progenitor cells or by induced pleuripotent stem cells. Furthermore different sub-populations or subsets of mesenchymal stem cells may be more efficient at secreting one or a number of these proteins, than another subset and different subsets may be more efficacious than a mixed mesenchymal stem cell population. Accordingly the source of the protein may vary and the source is not limited to bone marrow derived cells.

In one aspect of the present invention, there is provided a pharmaceutical composition comprising mesenchymal stem cells which express or over-express one or more proteins selected from the group comprising Sparcl1, Sfrp2, Fgl2, TEK, Angptl4, Notch1, Podxl, Lama2, Cthrc1, Cxcl 10, Il 1α, and Ifn g, and a pharmaceutically acceptable carrier or excipient. The cells may be mesenchymal stem cells, endothelial progenitor cells or induced pleuripotent stem cells. The cells may be encapsulated by methods known in the art to increase biocompatibility.

It may be desirable that the cells are transfected with a vector comprising one or more genes encoding one or more of the proteins Sparcl1, Sfrp2, Fgl2, TEK, Angptl4, Notch1, Podxl, Lama2, Cthrc1, Cxcl 10, II 1α, or Ifn g. Overexpression of one or more of the proteins by cells can be achieved in a variety of ways known to the person skilled in the art, for example by transfecting the cell with liposome or adenovirus encoding those proteins.

Under hypoxic conditions such as those occurring during ischemic and vascular episodes, and myocardial infarction, the expression of a number of genes, such as Sfrp2, Sparcl1, TEK, and Angptl4, are significantly increased which demonstrates that the increase in expression is not due to hypoxia alone but may be the result of their interactions, for example, with resident cardiomyocytes in the damaged heart. In myocardial complications apoptosis has been observed repeatedly in compromised human hearts and has been proven to be a major contributor to cardiomyocyte death during ischemic/reperfusion (I/R) injury and cardiomyopathy. The present invention has demonstrated that caspase activity, a hallmark of apoptosis, was decreased and mitochondrial activity increased in cardiomyocytes treated with adenovirally transduced MSCs and with media conditioned by adenovirally transduced MSCs. Such findings are unexpected and are a significant advance in therapeutic regimens for not just treating myocardial infarction but also other cardiovascular conditions and associated complications such as peripheral vascular disease, ischemia, cerebrovascular disease which may be due to the presence of risk factors for these vascular diseases such as diabetes mellitus, dyslipidaemia and hypertension.

In a further aspect, there is provided a pharmaceutical composition comprising cardiomyocyte-conditioned medium suitable for administration to a patient and a pharmaceutically acceptable carrier or excipient. By conditional medium we mean the medium in which such cells have been growing. The conditioned media may contain one or more proteins selected from the group comprising Sparcl1, Sfrp2, Fgl2, TEK, Angptl4, Notch1, Podxl, Lama2, Cthrc1, Cxcl 10, II 1α, and Ifn g. Surprisingly, the present invention has demonstrated that human aortic endothelial cells treated with conditioned media from MSCs adenovirally transduced with Sparcl1 exhibited enhanced angiogenesis and cardioprotection, including increased tubule formation. These findings suggest that such a treatment promises enhancement of in vivo neo-vascularisation to damaged myocardium.

In a further aspect of the present invention, there is provided a pharmaceutical composition comprising one or more genes selected from the group consisting of (a) nucleotide sequences encoding Sparcl1, Sfrp2, Fgl2, TEK, Angptl4, Notch1, Podxl, Lama2, Cthrc1, Cxcl 10, II 1α, and Ifn g, or (b) nucleotide sequences which hybridise under stringent conditions to the nucleotide sequences of (a) and encode the proteins having the activity of one or more of Sparcl1, Sfrp2, Fgl2, TEK, Angptl4, Notch1, Podxl, Lama2, Cthrc1, Cxcl 10, II 1α, and Ifn g, and a pharmaceutically acceptable carrier or excipient. Particularly preferred is Sparl1.

In another aspect of the present invention, there is provided the use of mesenchymal stem cells which express or over-express one or more proteins selected from the group comprising Sparcl1, Sfrp2, Fgl2, TEK, Angptl4, Notch1, Podxl, Lama2, Cthrc1, Cxcl 10, II 1α, and Ifn g, in the preparation of a medicament for the treatment of vascular disease and associated complications. The cells may be mesenchymal stem cells, endothelial progenitor cells or induced pleuripotent stem cells.

In a further aspect of the present invention, there is provided the use of one or more mesenchymal stem cell-secreted proteins selected from the group comprising Sparcl1, Sfrp2, Fgl2, TEK, Angptl4, Notch1, Podxl, Lama2, Cthrc1, Cxcl 10, II 1α, Ifn g, or combinations thereof, in the preparation of a medicament for the treatment of vascular disease and associated complications-, for wound healing and wound repair, particularly repair of heart tissue, for orthopaedic applications, treatment of degenerative joint disease and broken limb repair.

In a further aspect, there is provided the use of one or more genes encoding Sparcl1, Sfrp2, Fgl2, TEK, Angptl4, Notch1, Podxl, Lama2, Cthrc1, Cxcl 10, II 1α, and Ifn g in the preparation of a medicament for the treatment of vascular disease and associated complications for wound healing and wound repair, particularly repair of heart tissue, for orthopaedic applications, treatment of degenerative joint disease and broken limb repair.

There is also provided a method of treating vascular disease and associated complications comprising administering to a patient a pharmaceutically effective amount of a protein selected from the group comprising Sparcl1, Sfrp2, Fgl2, TEK, Angptl4, Notch1, Podxl, Lama2, Cthrc1, Cxcl 10, II 1α, Ifn g.

In one embodiment the invention provides a method of treating vascular disease and associated complications, for wound healing and wound repair, particularly repair of heart tissue, for orthopaedic applications, treatment of degenerative joint tissue and broken limb repair comprising administering to a patient a pharmaceutically effective amount of one or more nucleotide sequences selected from the group encoding Sparcl1, Sfrp2, Fgl2, TEK, Angptl4, Notch1, Podxl, Lama2, Cthrc1, Cxcl 10, II 1α, and Ifn g.

In a further embodiment, the invention provides method of treating vascular disease and associated complications, for wound healing and wound repair, particularly repair of heart tissue, for orthopaedic applications, treatment of degenerative joint tissue and broken limb repair comprising administering to a patient a which expresses or over-expresses one or more proteins selected from the group comprising Sparcl1, Sfrp2, Fgl2, TEK, Angptl4, Notch1, Podxl, Lama2, Cthrc1, Cxcl 10, II 1α, and Ifn g. The cell may be a mesenchymal stem cell, endothelial progenitor cells or induced pleuripotent stem cells. It may be desirable that the method comprises the step of administering to a patient one or more genes selected from the group consisting of (a) nucleotide sequences encoding Sparcl1, Sfrp2, Fgl2, TEK, Angptl4, Notch1, Podxl, Lama2, Cthrc1, Cxcl 10, II 1α, and Ifn g, or (b) nucleotide sequences which hybridise under stringent conditions to the nucleotide sequences of (a) and encode the proteins having the activity of one or more of Sparcl1, Sfrp2, Fgl2, TEK, Angptl4, Notch1, Podxl, Lama2, Cthrc1, Cxcl 10, II 1α, and Ifn g. A further aspect may be where the nucleotide sequence encoding Sparcl1, Sfrp2, Fgl2, TEK, Angptl4, Notch1, Podxl, Lama2, Cthrc1, Cxcl 10, II 1α, or Ifn g, or a combination thereof, is administered as part of a gene therapy technique. The cell may be a mesenchymal stem cell, endothelial progenitor cells or induced pleuripotent stem cells In a further aspect, the invention provides the use of one or more of Sparcl1, Sfrp2, Fgl2, TEK, Angptl4, Notch1, Podxl, Lama2, Cthrc1, Cxcl 10, II 1α, and Ifn g as angiogenic, cell migration, cytoprotective, and/or immunomodulating factors. It may be desired that the use comprises direct administration of Sparcl1, Sfrp2, Fgl2, TEK, Angptl4, Notch1, Podxl, Lama2, Cthrc1, Cxcl 10, Il 1α, and Ifn g, or genetically modified cells to over-express one or more of Sparcl1, Sfrp2, Fgl2, TEK, Angptl4, Notch1, Podxl, Lama2, Cthrc1, Cxcl 10, Il 1α, and Ifn g. The cells may be mesenchymal stem cells, endothelial progenitor cells or induced pleuripotent stem cells.

In one embodiment, the invention provides a medical device coated with (a) one or more recombinant proteins selected from the group comprising Sparcl1, Sfrp2, Fgl2, TEK, Angptl4, Notch1, Podxl, Lama2, Cthrc1, Cxcl 10, Il 1α, and Ifn g, (b) a vector comprising one or more genes encoding one or more proteins selected from the group comprising Sparcl1, Sfrp2, Fgl2, TEK, Angptl4, Notch1, Podxl, Lama2, Cthrc1, Cxcl 10, Il 1α, and Ifn g or (c) mesenchymal stem cells which over-express one or more proteins selected from the group comprising Sparcl1, Sfrp2, Fgl2, TEK, Angptl4, Notch1, Podxl, Lama2, Cthrc1, Cxcl 10, Il 1α, and Ifn g. The device may be selected from a stent, a suture, a dressing, a catheter, or a prothesis. However, any other medical device for delivering an active pharmaceutical ingredient may also be used. The pharmaceutical composition or the method may involve administration of the active agents via the pericardium, or by an intra-coronary or an intra-myocardial route. The method of administration may also be intravenous.

Where suitable, it will be appreciated that all optional and/or preferred features of one embodiment of the invention may be combined with optional and/or preferred features of another/other embodiment(s) of the invention.

DEFINITIONS

Sparcl-1 belongs to a group of matricellular proteins that are central in mediating cell-matrix interactions during tissue repair. It is also known as hevin, mast9, sc1, and ECM2. It is a component of the extracellular matrix produced by bone marrow stromal cells and preferentially binds to pre B cells. It influences migration, proliferation, shape and motility of cultured cells and is presumed to have a protective role for increased SPARC expression against cardiac dilation after myocardial infarction.

As used herein the term 'vascular diseases or complications' includes conditions such as myocardial infarction, heart failure, cardiovascular disease, peripheral vascular disease, ischemia of all organs, cerebrovascular disease which may be due to the presence of risk factors for these vascular diseases such as diabetes mellitus, dyslipidaemia and hypertension.

As used herein, the term "pharmaceutically acceptable carrier" or "excipient" is used to describe those components such as gums, coatings, binders, API's (active pharmaceutical ingredients), disintegrants, lubricants, disintegration agents, suspending agents, solvents, glidants, anti-adherents, anti-static agents, surfactants, plasticizers, capsules, emulsifying agents, and the like commonly used by those skilled in the art. The carrier or excipient can be in the form of fluid, capsule, tablet, pill, patch, and the like commonly used by those skilled in the art.

The "route of administration" of the compositions and medicaments of the present invention is used to describe administration by routes such as transdermal, transmucosal, topical (for example, epicutaneously), enteral (for example, orally), and/or parenteral (for example, intravenous, intraarterial, intramuscular, intracardiac, subcutaneously).

As used herein, the term "suitable for administration to a patient" refers administration of the active pharmaceutical ingredient and the carrier in which it is delivered, such as a pharmaceutically acceptable carrier, excipient or conditioned media, to a patient without the patient experiencing undue toxicity, irritation, allergic response, and the like, and effective for the intended use of the pharmaceutics.

The term "stringency" is used to describe the temperature, ionic strength and solvent composition existing during hybridization and the subsequent processing steps. Those skilled in the art will recognize that "stringency" conditions may be altered by varying those parameters either individually or together. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid.

With "high stringency" conditions, nucleic acid base pairing will occur only between nucleic acid fragments that have a high frequency of complementary base sequences (for example, hybridization under "high stringency" conditions, may occur between homologs with about 85-100% identity, preferably about 70-100% identity). With medium stringency conditions, nucleic acid base pairing will occur between nucleic acids with an intermediate frequency of complementary base sequences (for example, hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency" conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is used.

"Medium stringency" conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C., when a probe of about 500 nucleotides in length is used.

"Low stringency" conditions are those equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C., when a probe of about 500 nucleotides in length is used.

In the context of nucleic acid in-vitro amplification based technologies, "stringency" is achieved by applying temperature conditions and ionic buffer conditions that are particular to that in-vitro amplification technology. For example, in the context of PCR and real-time PCR, "stringency" is achieved by applying specific temperatures and ionic buffer strength for hybridisation of the oligonucleotide primers and, with regards to real-time PCR hybridisation of the probe/s, to the target nucleic acid for in-vitro amplification of the target nucleic acid.

An "nucleotide sequence" or "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

BRIEF DESCRIPTION OF THE DRAWINGS

Additional features and advantages of the present invention are described in, and will be apparent from, the detailed description of the invention and from the drawings in which:

FIG. 3(A) fluorescent imaging of engrafted PKH-26 MSCs prior to isolation;

FIG. 3(B) removal of MSCs from the border-zone of the infarcted myocardium using a thin pulsed laser. Isolated MSCs were retrieved mechanically using an adhesive lid;

FIG. 3(C) Gene expression profile of control MSCs v engrafted MSCs;

FIG. 3(D) Graphic representation of the top 10 most highly upregulated genes as determined by genespring analysis;

FIG. 3(E) RT-PCR validation of microarray targets;

DETAILED DESCRIPTION OF THE DRAWINGS

Figure 1:
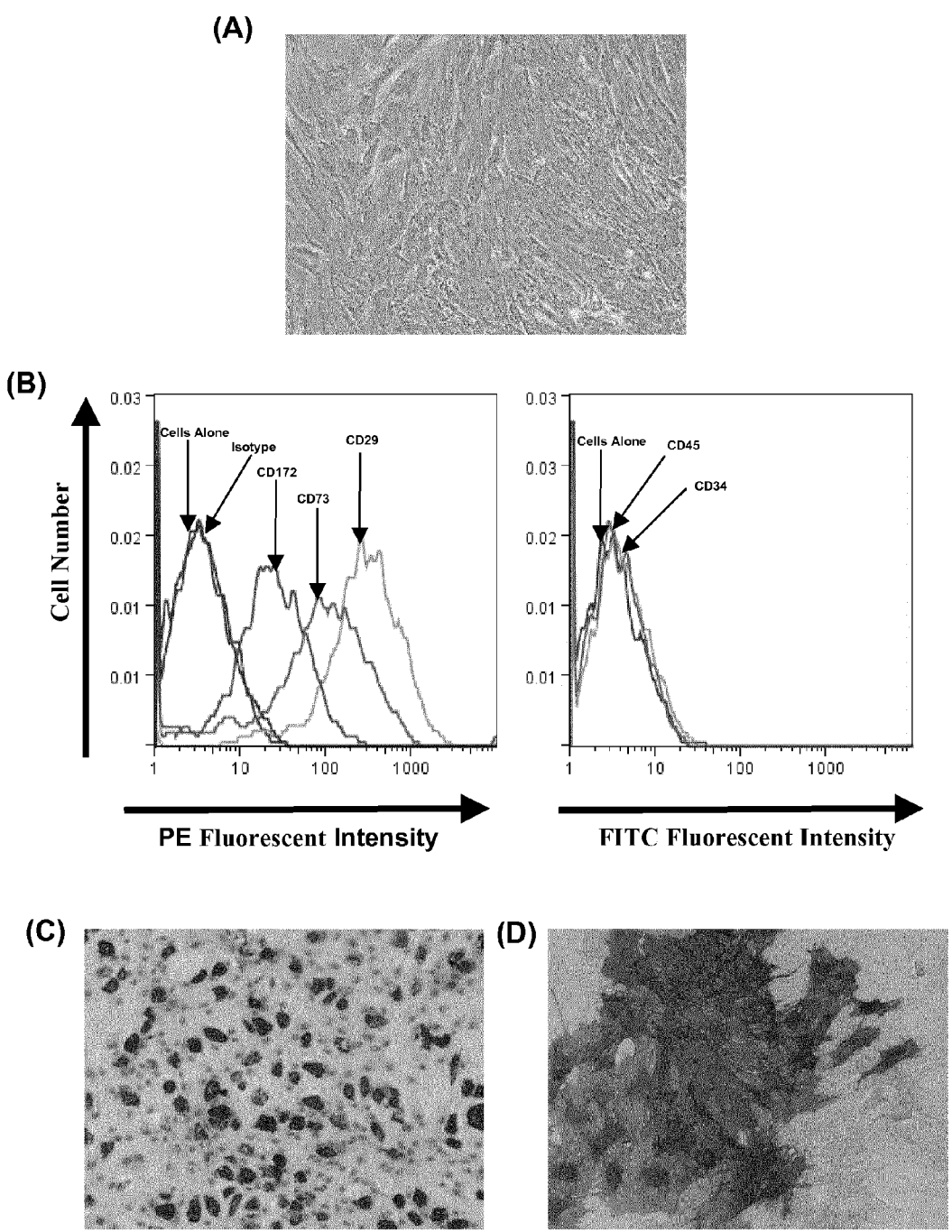
FIG. 1(A) to 1(D) Characterization of isolated mesenchymal stem cells illustrated by (A) direct plating of MSC to culture plastic, (B) cell marker profiles, MSC differentiated along (C) adipogenic and (D) osteogenic lineage after exposure to differentiation inductive media.
FIG. 1(E) to 1(I) Cell labeling and Delivery to the Myocardium after Infarct Induction illustrated by (E) complete ligation of left anterior descending (LAD) coronary artery, (F) infarct of left ventricle wall, (G) and (H) MSCs, labeled with cytoplasmic dye PKH-26, remain fibroblastic in morphology after cell loading, and (I) PKH-26$^+$ MSCs visualized in injection tracks in the border zone of the infarct 24 hours after direct intramyocardial injection (IMC injection)
Figure 1:
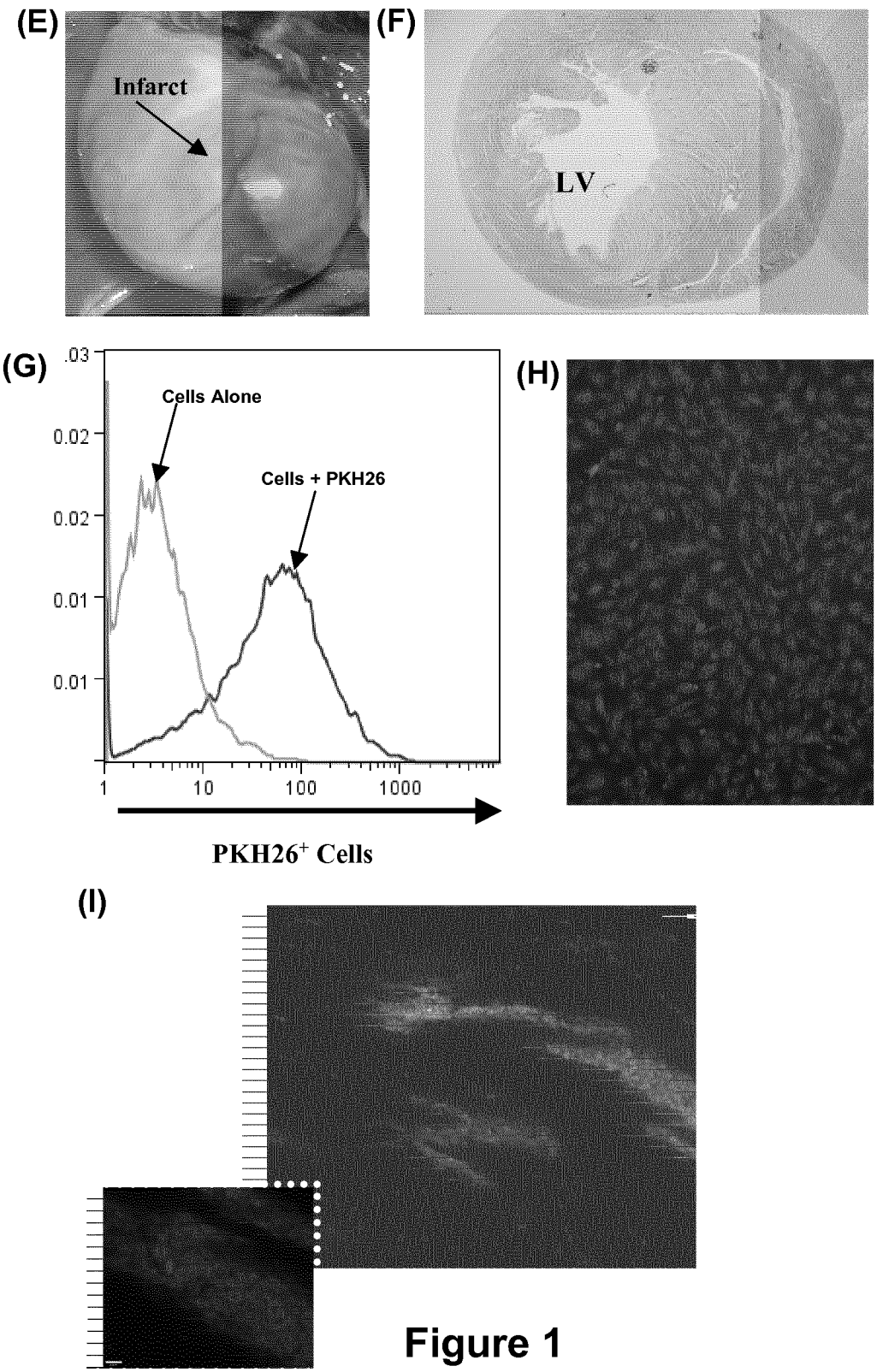

It should be readily apparent to one of ordinary skill in the art that the examples disclosed herein below represent generalised examples only, and that other arrangements and methods capable of reproducing the invention are possible and are embraced by the present invention.

Materials and Methods
Mesenchymal Stem Cell Isolation and Expansion

MSCs were isolated from 8 week old female Fischer 344 rats as described (Dobson 1999). After euthanasia, marrow was flushed from the tibia and fibula with phosphate buffered saline (PBS) and a single cell suspension was recovered. After centrifugation (600×g, 10 minutes) cells were plated at $120\times10^6$ cells/cm$^2$, in 10% fetal bovine serum (FBS; Hyclone), 45% F12-Ham and 45% α-MEM (Gibco) supplemented with antibiotics (100 U/mL penicillin G and 100 μg/mL streptomycin sulphate; Gibco). Flasks were incubated at 37° C. in 5% $CO_2$/90% humidity. After 8 days when colonies became compact cells were detached with 0.25% trypsin/EDTA and re-plated at 2000 cells/cm$^2$. Subsequently, cultures were passaged at 5-day intervals and expanded to passage 5 for experimentation. Differentiation assays were performed under defined culture conditions as previously described (Barry, 2001 #363; Mackay, 1998 #362).

Phenotype Analysis

For Fluorescent Activated Cell Sorting (FACS) analysis, $1\times10^5$ cells (retrieved or pre-injection) were incubated with the respective primary antibody conjugated to phycoerythrin (PE) [CD 29; CD73; CD71; CD105; CD172; (BD Pharmingen—1:100 dilution)] or Fluorescein (FITC) [CD 45 (BD Pharmingen); CD34 1:100 (Santa Cruz)], diluted in 5% mouse serum in PBS for 30 minutes at room temperature. The cells were washed and resuspended in PBS and analysed on the BD FACSCanto (Becton Dickinson). Histograms of cell number versus fluorescence intensity were recorded with 10,000 cells per sample and analysed using either Flow Jo (Tree Star Inc.) or WinMDI (Purdue University).

Infarct Model

Female Fischer 344 rats at 12-14 weeks of age (Harlan Laboratories) were anesthetised, intubated and mechanically ventilated at 90 breaths per minute. The heart was exposed via a left thoracotomy incision and the left anterior descending (LAD) artery was permanently ligated with a no. 6 Vicryl suture. Ten minutes post-MI, serum-free media (Gibco) containing the MSC suspension ($4\times10^6$ MSCs/250 μl) was injected directly into the myocardium (intramyocardial injection; IMC) at 5 different locations around the border-zone. The thoracotomy was closed and the rats were allowed to recover under supervision.

Labelling and Cell Delivery

MSCs were fluorescently labelled with PKH-26 at a final concentration of 250 μM 2× PKH-26 with minor modifications to the manufacturers guidelines. Briefly, MSCs (P4) were trypsinised, counted and resuspended to $4\times10^6$ cells in 500 μl of diluent C. MSCs were mixed with the fluorescent dye using a pipette and incubated for 5 minutes at room temperature in the dark with sample agitation every 1 minute. Labelling was quenched using complete MSC medium and the cells were centrifuged at 400×g for 5 minutes. For IMC injection, $4\times10^6$ cells were resuspended in 250 μl of F12-Ham serum free media. Labelled MSCs were injected at 5 points in the border zone surrounding the infarct (50 μl per injection) 10 minutes after complete ligation of the LAD.

Dissociation of Heart and Lungs

Hearts and lungs were dissected into ice cold Ca—Mg-free PBS (D-PBS; Gibco) and chopped finely into 5 mLs of cell dissociation agent [0.25% Trypsin-EDTA diluted 1:1 in non-enzymatic cell dissociation agent (Cascade Biologics) plus 1 mg/mL of type IV collagenase; (Liu, 1999 #92; Scutt, 1999 #93)]. Tissue pieces in dissociation agent were placed on an orbital shaker (80 rpm) at 37° C. for 4 hours to aid dispersion. The digestion was quenched with 2 volumes of F12-Ham/10% FBS. Cell isolates and tissue pieces were passed through a series of sterile filters (100-40 μm) to insure a single cell suspension. Cells were centrifuged for 10 minutes at 500×g and cell pellets were resuspended in 1 mL of F12 Ham. Cells were counted and viability measured using the Guava Viability assay and resuspended at $1.6\times10^5$ cells/mL of F12-Ham for subsequent sorting. Samples were maintained on ice until sorting.

Fluorescent Activated Cell Sorting

All cell sorting and analyses were performed on a FACSAria (Becton-Dickinson) using a 100 μm nozzle and a sheath pressure of 20 psi. 10 mM HEPES (pH 7.4) was added to the cell suspension to help maintain physiological pH during sorting. PKK-26$^+$ cells were excited using a 488 nm laser and detected with a 570/BP20 optical filter and visualised on dot plots of PE vs. FITC, where negative fluorescent cells (heart cells) were considered FITC positive to allow for compensation between the two fluorescent cell populations. Increasing the PE amplification signal and compensating PE minus FITC allowed the population to be further separated. A gate was set around the identified PKH-26$^+$MSCs and cells were sterile sorted from dissociated hearts into complete MSC growth medium. Successful sorted cell counts were recorded and plates containing sorted cells were placed in an incubator at 37° C. in 5% CO2/90% humidity. Media was changed after 4 days and twice weekly thereafter. Dead cells were excluded by gating on forward and side scatter. Prior to sorts, 6-well plates containing 5 mL of complete MSC media were kept in an incubator to maintain pH. During sorts plates were at room temperature in a sealed filtered environment to insure sterility.

Laser Microdissection

Consecutive heart tissue sections were cut onto membrane slides for LMD (Molecular Machines and Industries (MMI)). Membrane slides were stored at −80° C. in the presence of a dessicant to dehydrate the sections and to preserve the RNA. Representative sections were taken for histological analysis. All LMD was performed at 40× magnification to ensure accurate positioning of the laser thereby avoiding sample contamination with non-target tissue. All consumables used during LMD were supplied by MMI unless otherwise stated.

Retrieval of the engrafted MSCs was performed using an MMI cellcut laser microdissection system. A thin pulsed UV laser was used to cut around the engrafted MSCs which were captured by an adhesive lid. Following tissue collection the MSCs were removed from the adhesive cap by vortexing and mixing the sample with buffer RLT (Qiagen) containing β-mercaptoethanol to lyse the cells. Cultured MSCs (P4) in monolayer were used as a control in this experiment.

RNA from all samples was isolated using the RNeasy Micro Kit (Qiagen) and subsequently run on the Agilent bioanalyser to determine the quantity and quality of the control and microdissected samples. Sample purity and concentration was assessed on a gel electrophoregram (Agilent). Only samples with a RNA Integrity Numbers (RIN) from 7 to 10 were suitable for downstream analysis. Retrieved MSC samples and control MSC samples were processed for microarray analysis by Almac Diagnostics (Belfast, UK).

Microarray Analysis

All sample preparations using the NuGEN Ovation RNA Amplification System V2 in combination with the FL-Ovation cDNA Biotin Module V2 were carried out in accordance with the guidelines detailed in the corresponding NuGEN technical manual. 50 ng of total RNA was amplified using the NuGEN WT-Ovation FFPE RNA Amplification System. First-strand synthesis of cDNA was performed with a unique first-strand DNA/RNA chimeric primer mix, resulting in cDNA/mRNA hybrid molecules. Following fragmentation of the mRNA component of the cDNA/mRNA molecules, second-strand synthesis was carried out and double-stranded cDNA was generated with a unique DNA/RNA heteroduplex at one end. In the final amplification step, RNA within the heteroduplex was degraded using RNaseH, and replication of the resultant single-stranded cDNA was achieved through DNA/RNA chimeric primer binding and DNA polymerase enzymatic activity. The amplified single-stranded cDNA was purified using the Zymo Research Clean and Concentrator-25 kit and assessed using spectrophotometric methods in combination with the Agilent Bioanalyzer. 5 μg of amplified single-stranded cDNA was fragmented and labelled using the FL-Ovation cDNA Biotin Module V2. The enzymatically and chemically fragmented product (50-100 nt) was labelled via the attachment of biotinylated nucleotides onto the 3'-end of the fragmented cDNA. The resultant fragmented and labelled cDNA was added to the hybridisation cocktail in accordance with the NuGEN guidelines for hybridisation onto Affymetrix GeneChip arrays. Following hybridisation for 18 hours at 45° C., the array was washed and stained on the GeneChip Fluidics Station 450 using the appropriate fluidics script, before being inserted into the Affymetrix autoloader carousel and scanned using the GeneChip Scanner 3000.

Bioinformatics and Data Analysis Methodology

Non linear polynomial curve fitting, using convergence of four replicates with a general formula of:

$$Y = a0 + a1X1 + a2X2 + \ldots + an-1X^{n-1}$$

was used to create a fifth replicate as a means for estimation of the overall average of gene expression and estimation of the fold change later in the analysis. The data points of replicates were scaled to the polynomial curve fitted value for control and treatment separately. The background corrected data were normalized by per-chip, per-gene and the global median polishing normalization method using GeneSpring bioinformatics software (GeneSpring GX 7.3.1, Silicon Genetics). Statistical analysis was based on the significance analysis of microarrays (SAM) algorithm implementing multiple t-tests, considering false discovery rate (FDR) estimated using R-Bioconductor integrated module[Y]. Estimated Q-values, as a measure of significance then converted to P-Values for the ease of reading. Gene filtering on normalized intensity using a >2-fold cut-off and P-Value cut off of <0.01 was used to generate list of genes for expression profiles of engrafted versus control MSCs. Functional clustering of lists of differentially expressed genes were generated by comparing them against the ontology terms for molecular function, cellular composition and biological processes using Gene Ontology databases (GO) and the Medical Subject Heading Terms Database.

Microarray Validation

Each microarray sample was processed for quantitative RT-PCR validation. Briefly, 10 ng of each RNA sample was converted to cDNA using the high capacity reverse transcription cDNA kit (Applied Biosystems). To amplify targets of interest in cDNA samples, a pre-amplification step was performed to increase the quantity of cDNA target expression using Taqman gene expression assays. Pre-amplification products were used as templates for the quantitative RT-PCR reaction and mixed with Taqman gene expression master mix prior to PCR. $\Delta Ct$ and $\Delta\Delta Ct$ of each gene expression assay were used to calculate gene expression and were expressed as fold change in expression when compared to control MSC samples. Microarray validation was performed using relative gene expression calculated using the $2^{\Delta\Delta Ct}$ method, normalised to the house-keeping gene Gas 6.

Hypoxia Culture Conditions

MSCs at passage 4 (P4) were seeded at a density of 5,000 cells/cm$^2$ on tissue culture plastic and incubated in hypoxic conditions (0.5% $O_2$:94.5% $N_2$:5% $CO_2$ at 37° C.) for 96 hours in a hypoxic chamber (Ruskinn Technologies). Control MSCs were maintained in traditional culturing conditions (21% $O_2$:5% $CO_2$ at 37° C.) for 96 hours. MSCs were then trypsinised, lysed using Trizol reagent (Invitrogen) and RNA was isolated using the RNeasy mini kit (Qiagen). Additionally, cardiac tissue biopsies were harvested from control non-infarcted heart tissue and infarcted heart tissue 1 week post MI. Tissue biopsies were homogenised using a tissue disruptor (Qiagen), lysed with Trizol reagent and RNA was isolated using the RNeasy mini kit according to manufacturer's guidelines. RNA (1500 ng) was reverse transcribed to cDNA using the high capacity cDNA reverse transcription kit (Applied Biosystems). cDNA (75 ng) was added to each RT-PCR reaction and gene expression was normalised to the endogenous control, GAPDH.

Matrigel Tubule Formation Assays

Human aortic endothelial cell (hAEC) tubule formation on Matrigel was carried out as described previously with modifications (Liu, et al 2002). All tissue culture plastics coming in contact with Matrigel were chilled prior to use to avoid early polymerisation of the Matrigel. Growth factor reduced Matrigel (150 μl/well; BD Biosciences) was coated onto the surface of a 48 well plate and was allowed solidify during a thirty minute incubation at 37° C. hAECs were trypsinised, counted and resuspended in normal endothelial growth medium and plated in each well at a density of $3.5 \times 10^4$ hAECs/100 μl. Cell suspensions were allowed to incubate for 24 hours with periodic imaging at 6, 12 and 18 hours. Tubule formation was imaged using the Olympus IX71 microscope and tubule length and number were calculated using Analysis D software.

The total tubule length following recombinant protein treatment was assessed by measuring total tubule length in 5 random fields. Recombinant protein (50 ng/ml) diluted in endothelial growth media was selected as the optimum protein concentration for TEK (a protein tyrosine kinase receptor for angiopoietin 1), Angptl4 (angiopoietin-like 4) and Sparcl1 (secreted protein acid-rich in cysteine-like 1) (R&D Systems). In all experiments, normal endothelial growth media was used as a control. CM from normal MSCs or Adenoviral Sparcl1 (AdSparcl1) transduced MSCs were additionally cultured on Matrigel to determine their effect on tubule formation. CM from either MSCs or AdSparcl1 transduced MSCs was added to hAEC cell suspensions for up to 24 hours and tubules were imaged periodically as described above. A neutralizing antibody for Sparcl1 protein was added to AdSparcl1 CM at varying concentrations (1 μg/ml & 2 μg/ml) as necessary. AdSparcl1 CM alone was used as a positive control.

Neonatal Cardiomyocyte Isolation and Culture

Neonatal cardiomyocytes were prepared and cultured as reported previously (Simpson, et al 1982). Briefly, 1-4 day old Fischer 344 rats were sacrificed and the hearts were excised, homogenized and subjected to overnight trypsin (Langanbach Services) digestion at 4° C. Trypsin inhibitor and collagenase (Langanbach Services) were added to digest the extracellular matrix prior to differential centrifugation through a discontinuous Percoll gradient. The middle layer of cells was collected, washed and resuspended in complete cardiomyocyte media consisting of DMEM/F-12 supplemented with 10% newborn fetal calf serum, 100 μM 5-bromo-2-deoxyuridine (BrDU), 1% insulin transferrin sodium selenite (ITS) liquid supplement media, 1 mM sodium pyruvate (Gibco), 1% antibiotic/antimycotic. The cell suspension was then counted and plated at a density of $1\times10^5$ cells/ml on 0.2% gelatin pre-coated flasks (Corning). Following two days in culture with media supplemented with 100 μm BrDU, cardiomyocytes were maintained in complete cardiomyoctye media. Media was changed every other day and cells were used for experimentation between 7-14 days of isolation.

Cardiomyocyte Conditioned Media (CM) Treatment of MSCs

Neonatal rat cardiomyocytes were isolated and cultured as described above. MSCs were plated in 100 mm cell culture dishes at a seeding density of $2.5\times10^4$ MSCs/cm$^2$ in complete MSC media and cultured for 24 hours. Following two days of culture, the conditioned media (CM) from cardiomyocyte cultures was removed and transferred to MSC cultures. Four treatment groups were used—MSCs continually cultured in complete MSC media, MSCs cultured in cardiomyocyte CM, MSCs cultured under hypoxic conditions for 96 hours in complete MSC media, hypoxic MSCs cultured in hypoxic cardiomyocyte CM for 96 hours. MSCs were expanded in the above media for 96 hours prior to cell harvest. All MSC samples were lysed in Trizol reagent (Invitrogen) and RNA was isolated using the RNeasy mini kit.

Sparcl1 Immunofluorescence

Cardiac tissue (8 μm) explanted 1 week post MI was cryo-sectioned and MSCs were located throughout the myocardium by positive staining with PKH-26. Adjacent heart tissue sections were stained for Sparcl1 localisation. Briefly, tissue sections were fixed for 15 minutes with 4% PFA and permeabilised for 2 minutes with 0.5% Triton X. Tissue sections were washed with PBS and blocked in 20% donkey serum for 1.5 hours. Tissue sections were incubated with Sparcl1 antibody (R&D Systems) in 10% serum in 0.5% BSA at a final concentration of 2 ng/ml. Secondary antibody (1:500; Molecular Probes) incubation was followed by staining with the nuclear DAPI stain and slides were mounted with DAKO mounting media. Goat IgG antibody was used as an isotype control. Fluorescence imaging was conducted using the Olympus IX71 microscope. Pseudo-confocal images were taken with a Zeiss Observer Z.1 using Axiovision 4.7 with deconvolution software.

MSC Transduction with Sparcl1 Adenovirus

AdSparcl1 virus production was performed by GeneCust Europe. Briefly, a first generation adenovirus vector containing the Sparcl1 gene was amplified through successive rounds of transduction in the complimentary Human Embryonic Kidney 293 (HEK 293) cell line and purified by ultracentrifugation on a cesium chloride density gradient. After buffer exchange, the vector was stored in 10% glycerol at −80° C. and titred by plaque assay determining plaque forming units (PFU) and optical density (OD) determining viral particles.

MSCs were transduced with AdSparcl1 using the spin method. Briefly, MSCs were plated at $2\times10^5$ MSCs/well in 6 well plates. AdSparcl1 with a titre of $1.4\times10^{10}$ pfu/ml was added to the MSCs in 500 μl of BM. Plates were spun at 37° C. for 1.5 hours at 2,000 g. Following centrifugation, 2 mls of complete MSC media was added to each well and cells were cultured at 37° C. Medium was changed 24 hours following transduction. Western blot analysis was performed to confirm Sparcl1 over-expression in adenovirally transduced MSCs and AdSparcl1 MSC CM.

Cardioprotection Assays

Following isolation, cardiomyocytes were plated at $1\times10^5$ cells/ml in 6 and 12 well tissue culture plates (Corning). Cardiomyocytes were allowed to adapt to normal tissue culture conditions for 5-8 days before experimentation. For hypoxic culture, complete cardiomyocyte media was depleted of $O_2$ by pre-incubation in hypoxic conditions (0.5% $O_2$; 94.5% $N_2$; 5% $CO_2$; 37° C.) for 3 hours before its addition to cultured cardiomyocytes. Cardiomyocytes were cultured under hypoxic conditions for 24 and 48 hours with our without the presence of Sparcl1 recombinant protein. To assess mitochondrial activity of cardiomyocytes following exposure to hypoxia, MTT assays were carried out.

Cardiomyocyte samples were also assessed for caspase activity. Following 48 hours exposure to hypoxia, cardiomyocytes were scraped into their media and added to 15 ml tubes. Cell suspensions were centrifuged at 500 g for 5 minutes and the supernatant was removed. Pellets were then resuspended in 110 μl of lysis buffer (50 mM Hepes/KOH pH 7.2, 5 nM EGTA, 10 mM KCl, 2 mM $MgCl_2$, 2 mM Dithiothreitol (DTT) and 0.1% CHAPS). Immediately prior to sample reading, 100 μl of 2× substrate buffer (Biomol) was added to each well. The enzyme activity was determined by the rate of increase in fluorescence divided by the protein content per well to normalise caspase activity.

To determine the paracrine effects of MSCs and AdSparcl1 transduced MSCs on cardiomyocyte protection following exposure to hypoxia, CM was collected from both MSCs and AdSparcl1 transduced MSCs and transferred to cardiomyocytes prior to hypoxia exposure. Hypoxia exposure was conducted for 48 hours after which time cells were harvested for MTT and caspase assays as described above.

Statistical Analysis

The data obtained were assessed for statistical differences using a paired t test to compare experimental characteristics to control. All values are presented as the mean±standard error of the mean (SE). A level of $p<0.05$ was considered statistically significant.

Results

MSCs were Isolated from the Tibia and Fibula of Female Fischer 344 Rats and Expressed Characteristic MSC Markers.

Cell isolation and expansion from the rat tibia and fibula using direct plating was established according to previous reports (Dobson, 1999). Isolated MSCs adhered to culture plastic, had a fibroblastic morphology (FIG. 1A) and proliferated up to passage five (P5) with a doubling time of approximately 1.8 days. The isolated MSCs were negative for CD34 and CD45, known hematopoeitic markers, but were positive for markers characteristic of MSCs (CD29, CD105 and CD 172; FIG. 1B). The expanded cells differentiated along the adipogenic and osteogenic lineages after exposure to differentiation inductive media (FIGS. 1C and 1D).

Cell Labelling and Delivery to the Myocardium after Infarct Induction.

Complete ligation of the left anterior descending coronary artery caused immediate blanching of the left ventricle (FIG. 1E) and resulted in an infarct of approximately 60% of the left ventricle wall (FIG. 1F). MSCs were successfully labelled with the fluorescent cytoplasmic dye PKH-26 and remained fibroblastic in morphology after cell loading (FIGS. 1G & H). MSC viability was unaffected by labelling with 250 μM of PKH-26 (89.4%±3.1%; data not shown).

PKH-26⁺MSCs were visualised in injection tracks in the border zone of the infarct 24 hours after direct intramyocardial injection (FIG. 1I).

Retrieval of PKH-26⁺MSCs from the Myocardium 3 and 7 Days after Direct Intramyocardial Injection.

Figure 2:
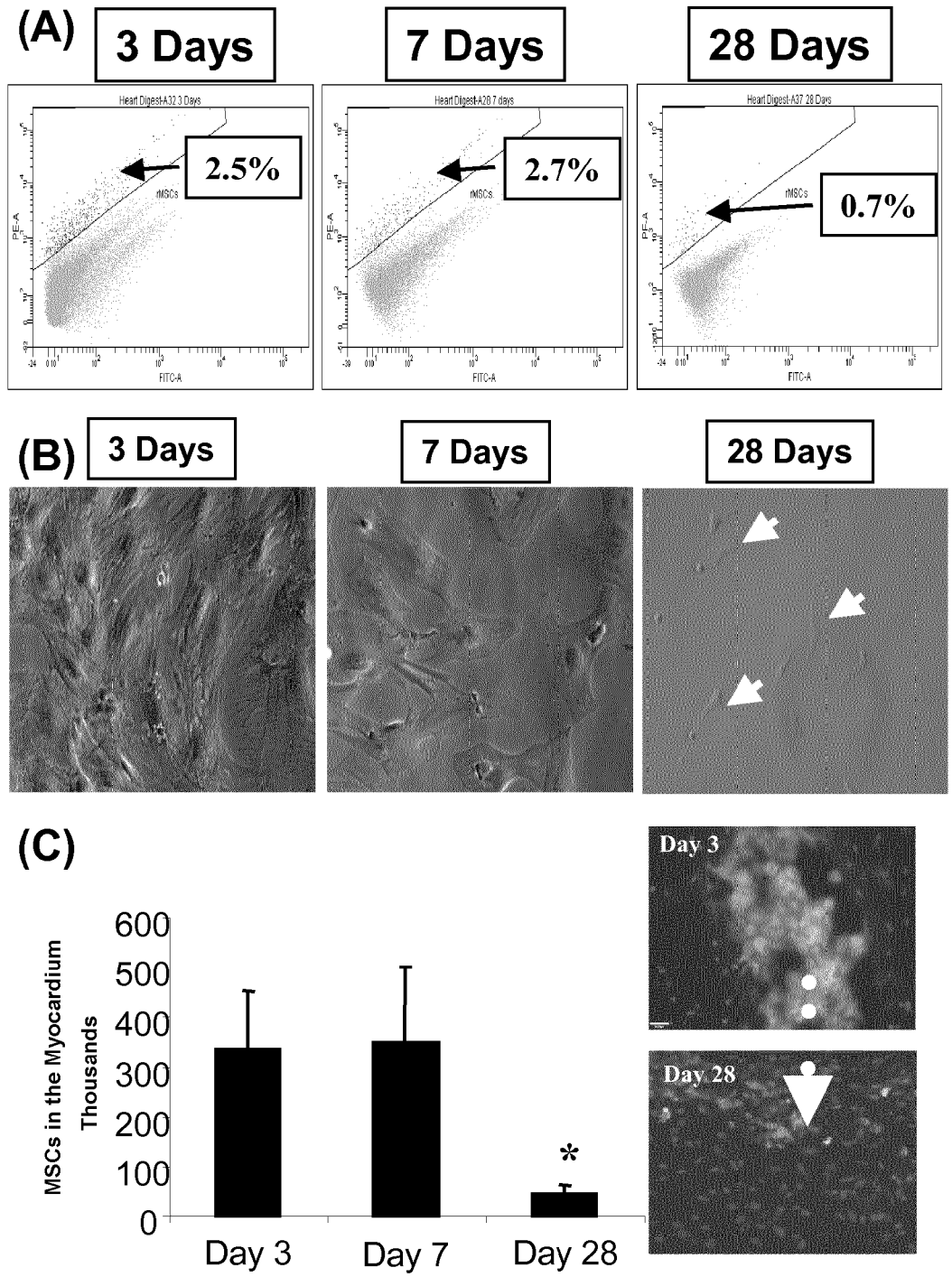
FIGS. 2(A), (B), and (C) illustrate the presence of PKH-26$^+$ MSCs in the heart on days 3, 7 and 28 after IMC delivery as represented by FACs analysis, culture of the cells, and cell counts, respectively.
FIG. 2(D) to 2(G) illustrate the expression of characteristic MSC markers at days 3 and 7 post-IMC injection and the differentiation potential of retrieved cells compared to pre-injected MSCs.
Figure 2:
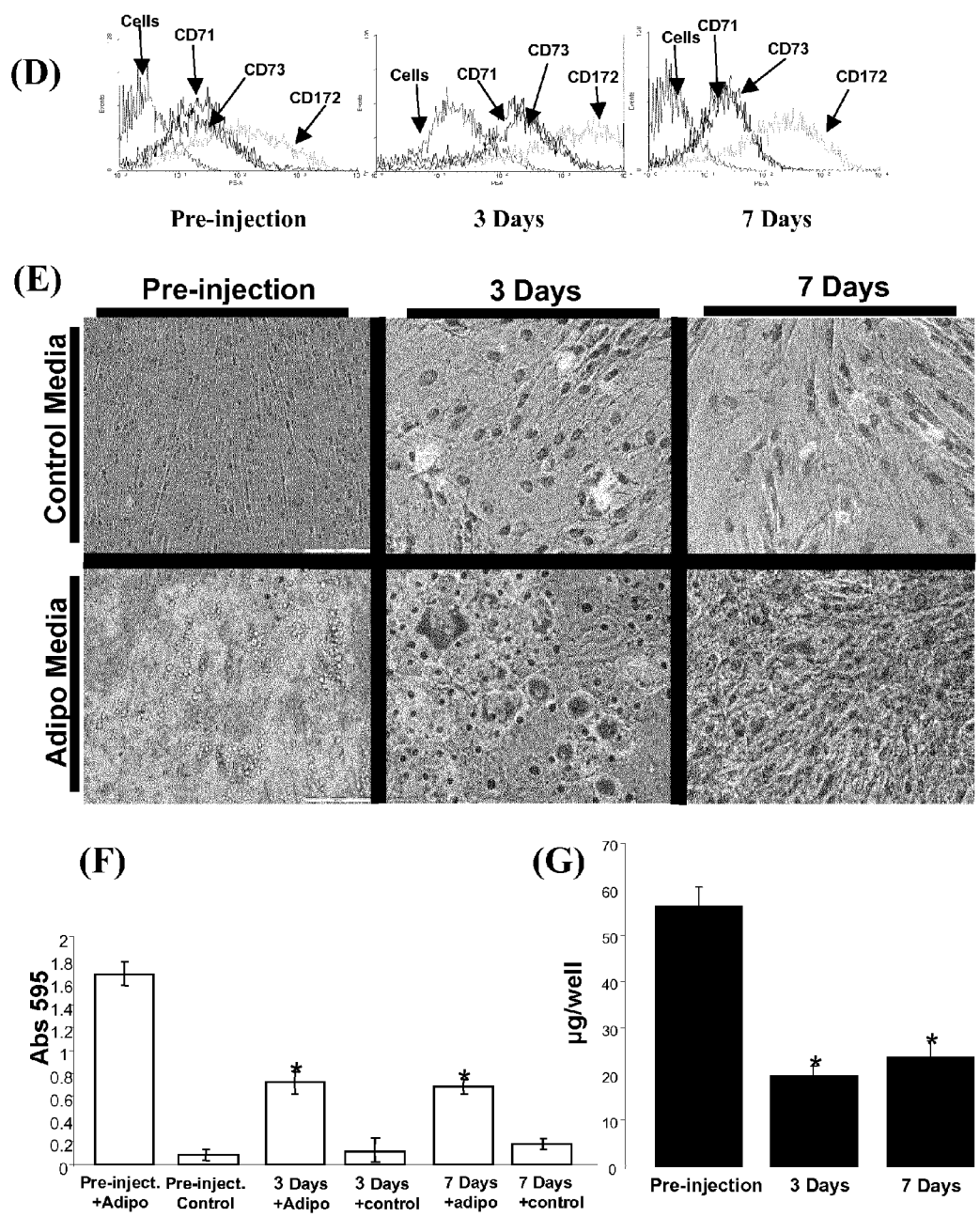

To investigate whether MSCs remain resident in the myocardium over time, the presence of PKH-26⁺MSCs in the heart on days 3, 7 and 28 after IMC delivery was examined. Cells were present in the heart at all three time points (FIG. 2A). Retrieved cells from day 3 and 7 hearts had a MSC-like morphology and were capable of being expanded in culture (FIG. 2B). Cells retrieved after 28 days also had a fibroblastic morphology in culture but did not expand to the same degree as cells retrieved at day 3 and day 7 (FIG. 2B, white arrows). When Comparing PKH-26⁺MSC numbers in the heart at day 3, 7 and 28 days it was evident that there was a large reduction in cell number at the 28 day time point after IMC injection (FIG. 2C). This reduction in PKH26⁺-MSC number was further observed in heart sections over the same time period (FIG. 2C).

The retrieved cells from both 3 and 7 day time points had similar levels of expression of characteristic MSC makers (CD 71, CD73 & CD172) compared to pre-injected cells (FIG. 2D). When the differentiation potential of the retrieved cells was assessed it was found that those cells isolated at days 3 and 7 maintained adipogenic (FIG. 2E) and osteogenic potential but at a significantly lower level compared to pre-injected MSCs (p<0.05; FIGS. 2F & G).

MSC Retrieval, Microarray and Functional Clustering Analysis

Figure 3:
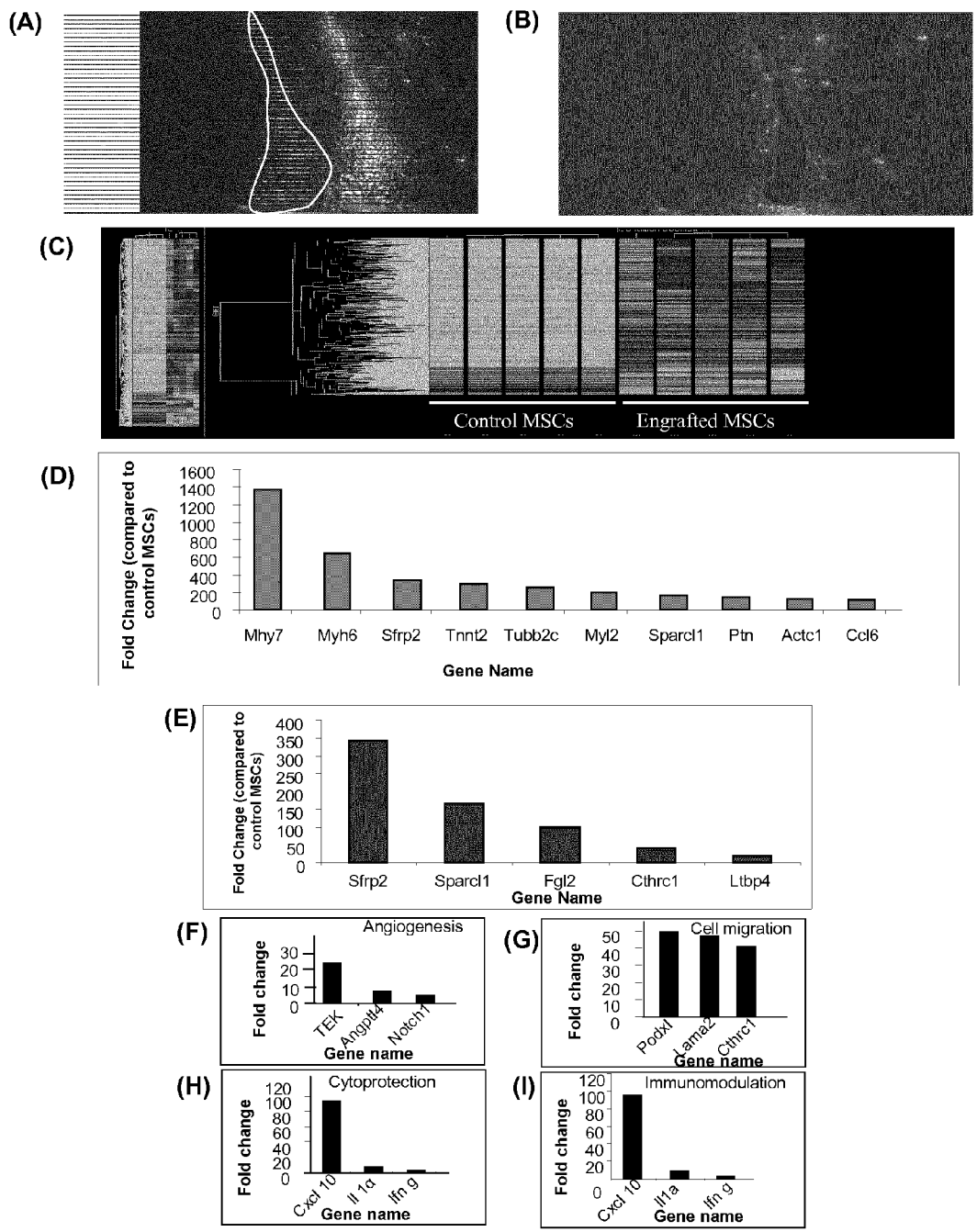
FIGS. 3 (F), (G), (H), and (I) Functional clustering of transcripts involved in angiogenesis, cell migration, cytoprotection, and immunomodulation, respectively.

Fluorescently labelled PKH-26+MSCs were identified as 'cell islands' in and adjacent to the injection site following IMC delivery (FIG. 3A). Using LMD, the fluorescent MSC cell population was retrieved from the surrounding cell population. Contact with the adhesive lid of the collection tube ensured successful retrieval of the isolated MSC population (FIG. 3B). Following microarray analysis, a total of 1202 genes were found to be dysregulated in the retrieved MSC population when compared to control monolayer MSCs using Genespring software (FIG. 3C). Bioinformatic analysis of the microarray data identified 987 genes that were found to have increased expression when compared to control and 207 genes had decreased expression. Ten of the most highly expressed genes found in the microarray are listed in FIG. 3D, namely Mhy7 (encoding the (3-myosin heavy chain), Myh6 (myosin heavy chain 6 or alpha myosin heavy chain), Srfp2 (secreted frizzled protein 2), Tnnt2 (troponin T type 2), Tubb2c (tubulin beta-2 chain), Myl2 (myosin light chain 2), Sparcl1, Ptn (pleiotrophin), Actc1 (alpha cardiac actin), and Cc16 (chemokine (C-C) ligand 6). Following functional cluster analysis, a number of genes encoding secreted proteins were identified (FIG. 3E), including Sfrp2, Sparcl1, Fgl2 (fibrinogen-like protein 2), Cthrc1 (collagen triple helix containing 1), and Ltbp4 (latent transforming growth factor beta binding protein 4). Further clustering analysis identified a number of gene categories involving a number of therapeutically relevant genes including those involved in angiogenesis (TEK, Angptl4, Notch1) (FIG. 3F), cell migration (Podxl (podocalyxin like protein), Lama2 (laminin alpha-2), and Cthrc1) (FIG. 3G), cytoprotection (Cxcl 10 (chemokine (C-X-C motif) ligand 10), Il-1 alpha (interleukin-1 alpha), and Ifn g (interferon gamma)) (FIG. 3H) and immunomodulation (Cxcl 10, Il-1 alpha, and Ifn g) (FIG. 3I).

Sparcl1 Expression in the Cardiac Microenvironment

Figure 4:
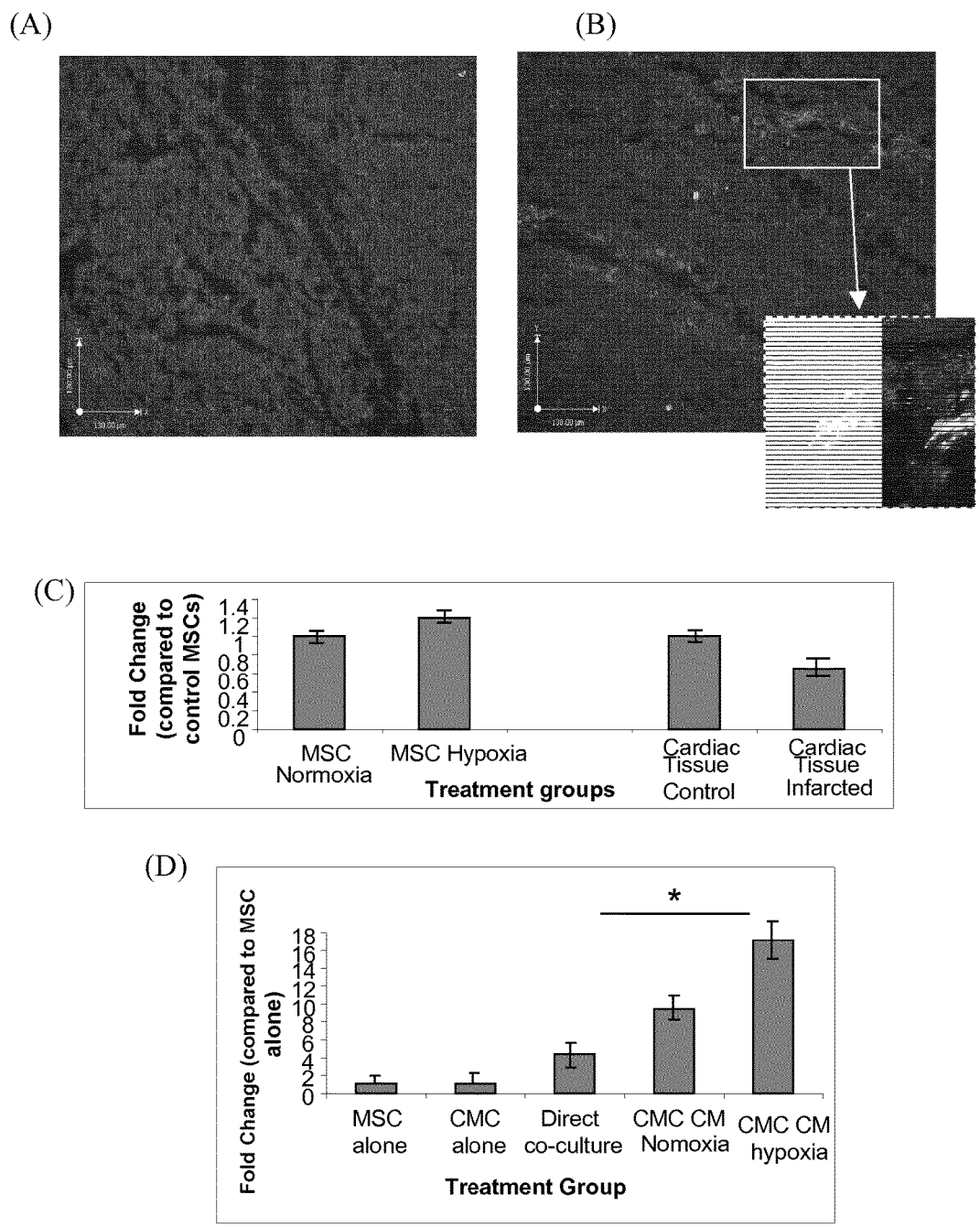
FIGS. 4(A) and (B) Immunofluorescence analysis of Sparcl1 localisation in the myocardium. (A) Sparcl1 expression following injection of control vehicle, F12-Ham. (B) Increased Sparcl1 expression was observed along the injection tract of engrafted MSCs as observed by the increase in FITC positive staining adjacent to the engrafted PKH-26 labelled MSCs (red)
FIG. 4(C) RT-PCR analysis illustrated no difference in Spracl1 expression in MSC cells following exposure to hypoxia and in infracted tissue when compared to control.
FIG. 4(D) Sparcl1 up regulation following direct and indirect culture with cardiomyocytes (Sparcl1 expression was calculated using the $2^{\Delta\Delta Ct}$ method expressed as a fold change when compared to control MSCs; error bars represent standard error of the mean (n=3), P<0.05 when compared to control MSCs)

To confirm the expression of Sparcl1 protein at the site of injection, immunofluorescent analysis of tissue sections was performed. Although Sparcl1 expression was constitutively observed throughout the myocardium, injection of vehicle into the border zone of the heart did not result in an increase of Sparcl1 expression (FIG. 4A). However, following delivery of PKH-26+MSCs to the infarcted zone, an increase in Sparcl1 expression was observed surrounding the injection track (FIG. 4B). High powered fluorescence microscopy confirmed co-localisation of Sparcl1 protein with the fluorescently delivered MSCs (FIG. 4B). To determine the source of Sparcl1 expression, a number of in vitro culturing methods were assessed. RT-PCR analysis of MSC following exposure to hypoxia did not result in an increase in Sparcl1 expression. Furthermore, Sparcl1 gene expression was not increased in infarcted cardiac tissue when compared to control (FIG. 4C). However, culture of MSCs either directly or indirectly with cardiomyocytes or cardiomyocyte CM, respectively resulted in an increase in Sparcl1 expression. Direct co-culture of MSCs with rat neonatal cardiomyocytes resulted in a 4-fold increase in Sparcl1 expression; however, this effect was enhanced when MSCs were incubated with cardiomyocyte CM alone. Repeating the indirect culture conditions under hypoxic conditions resulted in a 16-fold increase in Sparcl1 expression when compared to control MSCs (FIG. 4D).

Therapeutic Functionality of Sparcl1 Recombinant Protein Tubule Formation

Figure 5:
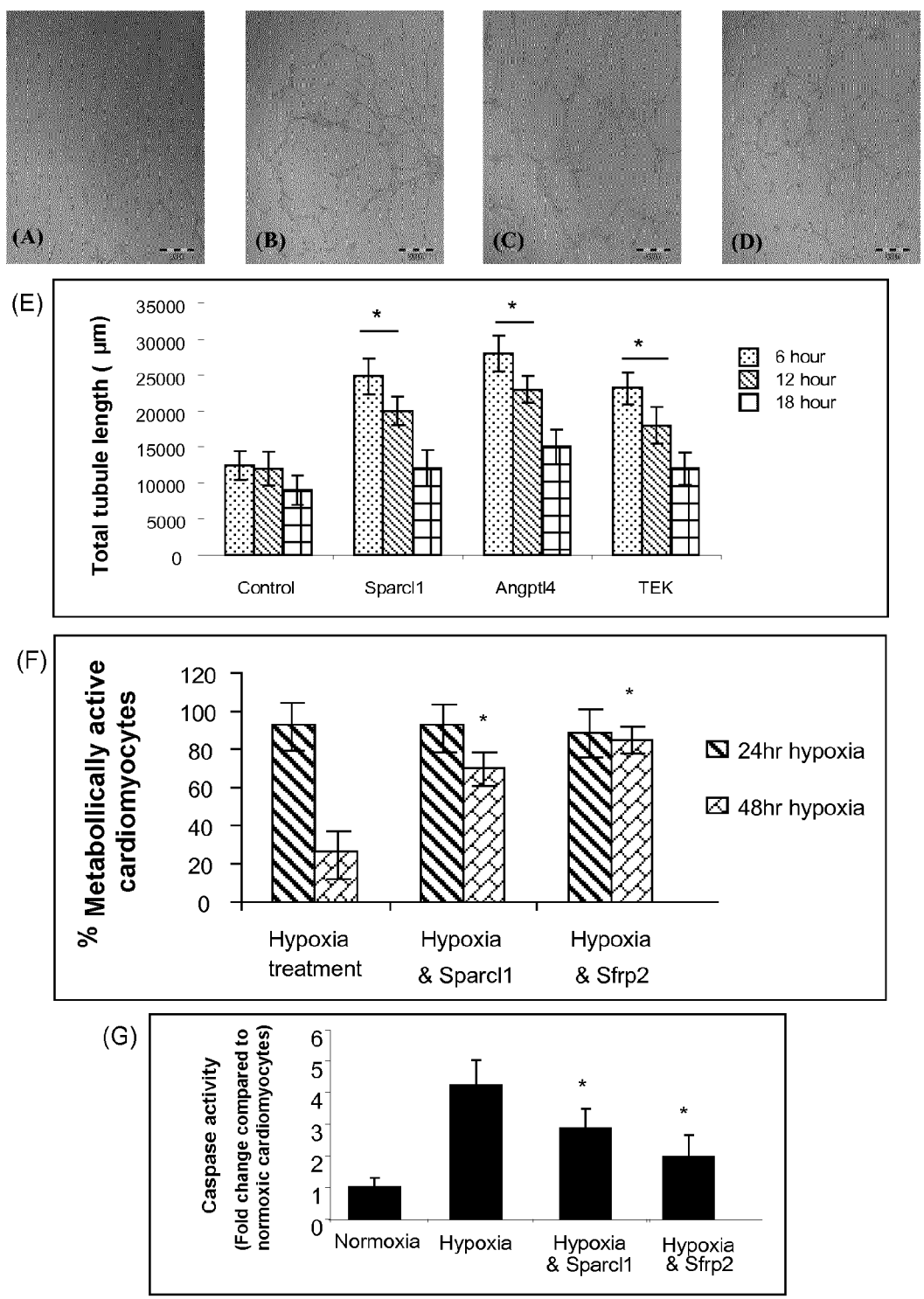
FIG. 5(A) to 5(E) Sparcl1, Angptl4 and TEK recombinant protein stimulated hAEC tubule formation illustrated by (A) hAEC cultures maintained in control medium, (B) hAEC cultures maintained in culture medium supplemented with Sparcl1 recombinant protein, (C) hAEC cultures maintained in culture medium supplemented with Angptl4 recombinant protein, (D) hAEC cultures maintained in culture medium supplemented with TEK recombinant protein, and (E) representative quantification of tubule length (µm) formed following EC plating after 6, 12, and 18 hours (Total tubule length was calculated be measuring the tubule length in 5 random fields; error bars represent standard error of the mean (n=3), *=P<0.05 when comparing all recombinant protein treatment groups to control endothelial growth medium)
FIGS. 5(F) and 5(G) Cardioprotection assays using Sparcl1 and Sfrp2 recombinant protein illustrated by a representative quantification of (F) MTT activity following 24 hour and 48 hour exposure to hypoxia and (G) caspase 3-like activity following 48 hours exposure to hypoxia.

To assess the role of Sparcl1 in angiogenesis, hAECs were treated with Sparcl1 recombinant protein. Tubule formation occurs naturally following the plating of hAECs onto growth factor reduced Matrigel (FIG. 5A), however it is significantly enhanced following the addition of Sparcl1 recombinant protein. Cellular branching was particularly evident with a strong lattice formation present following 6 hours in culture (FIG. 5B). Following treatment with Angptl4 recombinant protein, a closely related member to the angiopoietin-like family that have been extensively researched for their role in angiogenesis and arteriogenesis (Le Jan, et al 2003, Tressel, et al 2008), there is a significant increase in tubule length with increased branching of tubules compared to control (FIG. 5C). TEK, also known as Tie 2, has also been described for its role in angiogenesis and vasculogenesis (Slevin, et al 2009). Here, treatment of hAECs with TEK recombinant protein results in an increase in tubule formation, an improvement in vessel formation and a denser lattice structure when compared to control (FIG. 5D). In summary, the total length of tubules formed was significantly higher than control with a 2.5 fold, 3.6 fold, and 2.2 fold increase in hAEC tubule length observed after 6 hours of plating when treated with Sparcl1, Angptl4 and TEK recombinant proteins respectively (FIG. 5E). Subsequent analysis of tubule formation demonstrated a decrease in tubule length and break down of lattice structure out to 12 hours following hAEC plating. This observation was further enhanced 18 hours after plating with tubule lengths recorded similar to those observed in control groups (FIG. 5E).

Cardioprotection

Cardioprotection assays were carried out to determine the cytoprotective role of Sparcl1 recombinant protein. Cardiomyocytes treated with Sparcl1 protein were exposed to hypoxia after which cell death and viability was assessed using caspase and MTT assays. Cardiomyocytes cultured under hypoxic conditions for 24 hours showed only 12% cell death (FIG. 5F). To mimic the hypoxic insult suffered by resident cardiomyocytes following MI, cells were incubated in hypoxic conditions for 48 hours resulting in 47% of cardiomyocytes remaining mitochondrially active (FIG. 5F). Cardiomyocytes treated with Sparcl1 recombinant protein showed a 30% increase in mitochondrially active cells when compared to untreated cardiomyocytes under hypoxic conditions. Treatment of cardiomyocytes with Sfrp2 recombinant protein during hypoxia resulted in a 37% increase in cell viability when compared to untreated control (FIG. 5F).

Figure 7:
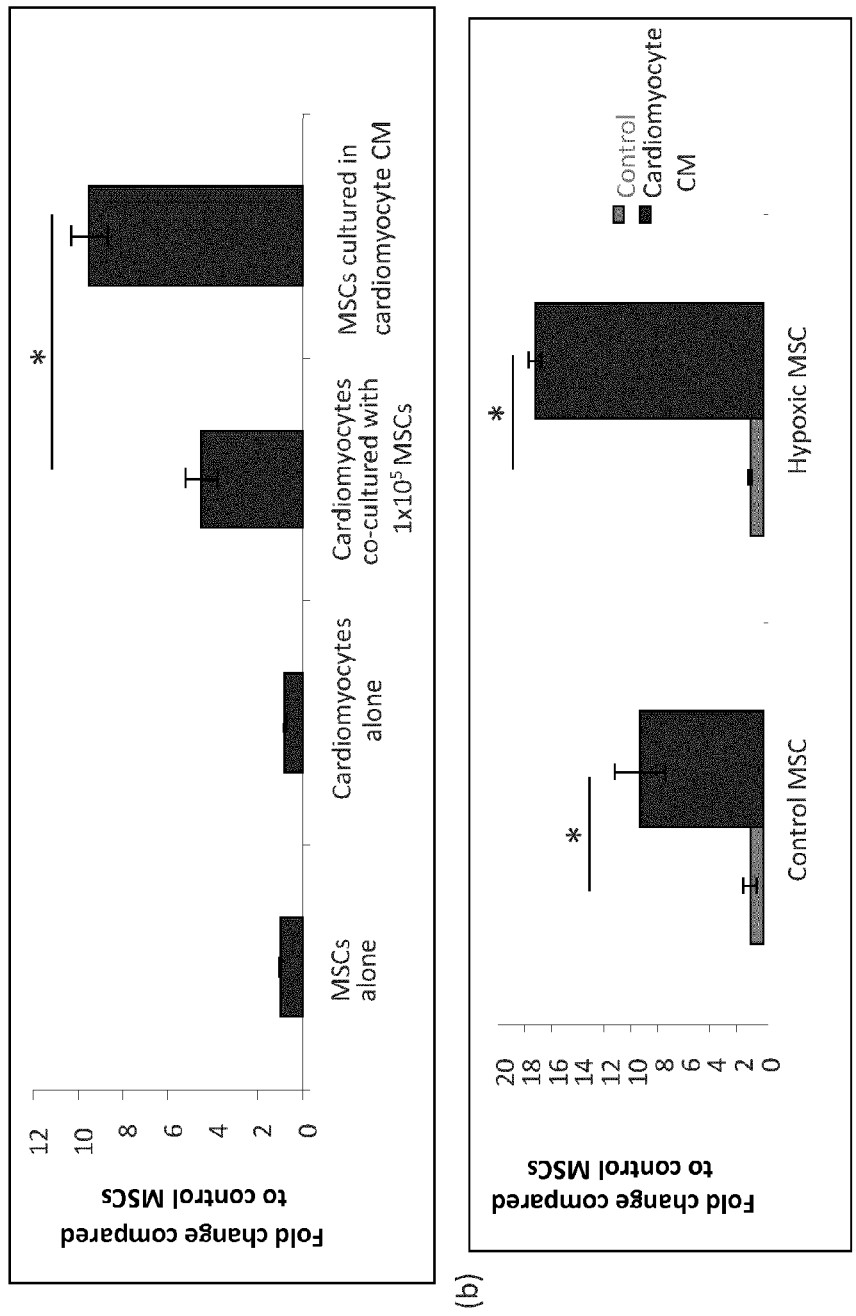
FIG. 7 shows up regulation of Sparcl1 in mesenchymal stem cell-cardiomyocyte co-culture. (a) and (b) show fold change in co-cultured cells compared to control mesenchymal stem cell cultures.
Figure 8:
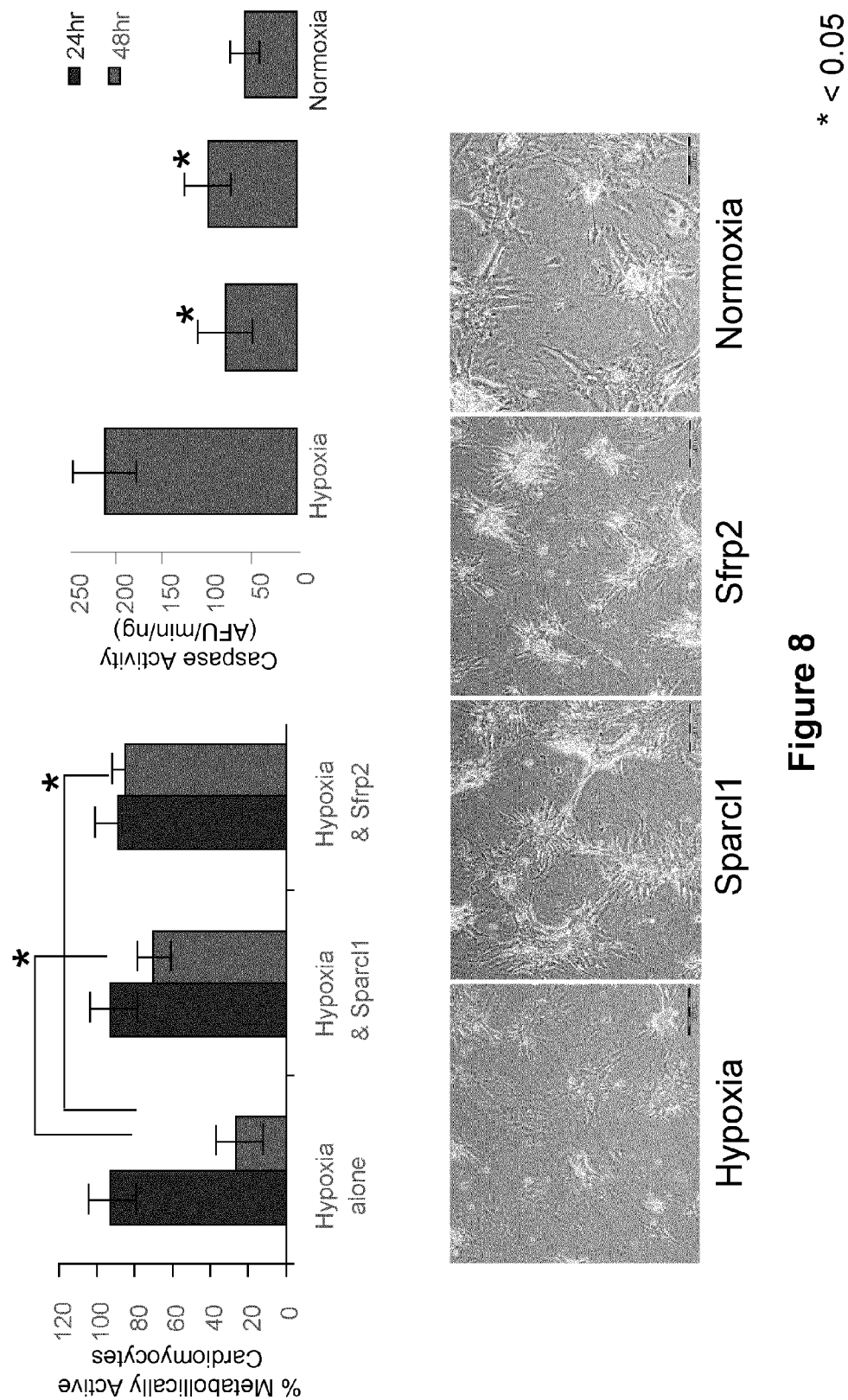
FIG. 8 Sparcl1 mediated cytoprotection on exposure to hypoxically injured cardiomyocytes.

Caspase activity in cardiomyocyte samples was also assessed following exposure to hypoxia. In this experiment staurosporine (STS), a known inducer of apoptosis was used as a positive control for apoptotic stimulation. Cells cultured under traditional culturing conditions were used as a negative control. Cardiomyocytes exposed to 48 hour hypoxia alone resulted in significant caspase activity when compared to normoxic cardiomyocytes. Following treatment of cardiomyocyte cultures with Sparcl1 recombinant protein, the level of caspase activity was reduced significantly resulting in a 1.6-fold decrease in caspase activity in treated cardiomyocytes (FIG. 5G) when compared to control. Treatment of cardiomyocytes with Sfrp2 protein also resulted in a reduction in caspase activity when compared to control demonstrating a 2-fold decrease in caspase activity (FIG. 5G). Similar results are shown in FIGS. 7 and 8.

Therapeutic Functionality of Adenoviral Transduced Sparcl1 Expressing MSCs.

Tubule Formation

Figure 6:
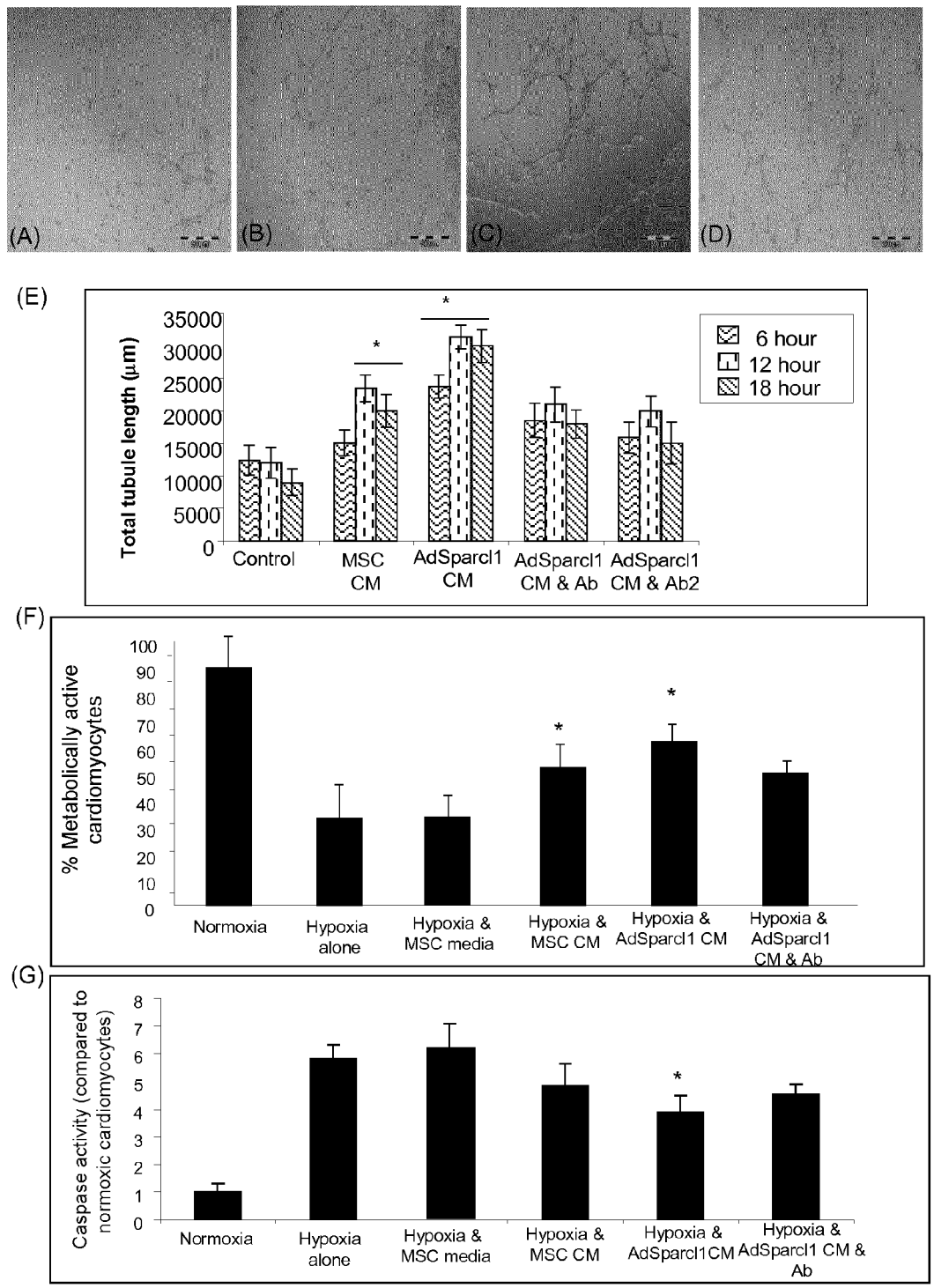
FIG. 6(A) to 6(E) Adenoviral transductions of MSC with Sparcl1 stimulate tubule formation illustrated by (A) control (complete endothelial cell medium), (B) 6 hours post-treatment with MSC CM alone, (C) AdSparcl1 transduced MSC CM treatment, (D) AdSparcl1 transduced MSC CM plus Sparcl1 antibody, and (E) representative quantification of total length of tubules formed following plating on growth factor reduced Matrigel after 6, 12, and 18 hours (Total tubule length was calculated be measuring the tubule length in 5 random fields; error bars represent standard error of the mean (n=3))
FIGS. 6(F) and 6(G) AdSparcl1 cardioprotection assays illustrated by a graphic representation of (F) metabolically active cardiomyocytes and (G) caspase activity by cardiomyocytes following exposure to hypoxic conditions for 48 hours (Error bars represent the standard error of the mean (n=3), *=P<0.05 when compared to cardiomyocytes cultured in hypoxia alone).

To assess the paracrine role of AdSparcl1 transduced MSCs in tubule formation, Matrigel assays were conducted using CM generated from AdSparcl1 MSCs. Incubation of hAECs with normal growth medium resulted in the formation of a low number of tubules and low levels of vessel sprouting (FIG. 6A). Treatment of hAECs with control MSC CM resulted in an increase in tubule number and length (FIG. 6B). hAECS were also treated with MSC normal growth media, however, despite the formation of a low number of tubules, tubule length and number remained low and MSC media did not support tubule growth following 12 hours in culture (data not shown). Treatment of hAECs with AdSparcl1 CM resulted in a significant increase in tubule formation. Tubule density was also increased and enhanced lattice formation was also observed when compared to control (FIG. 6C). To confirm the role of Sparcl1 protein specifically in tubule formation, a neutralising antibody was added at two concentrations to AdSparcl1 CM. Following antibody treatment, tubule density and frequency was reduced when compared to AdSparcl1 CM alone (FIG. 6D), suggesting a role for Sparcl1 in enhanced neovascularisation and angiogenesis.

Quantification of tubule length following 6, 12 and 18 hours of hAEC plating indicated a significant increase in tubule formation in hAECs cultured in both MSC CM and AdSparcl1 CM. Levels of tubule length were higher in AdSparcl1 CM treated hAECs compared to those cultured in MSC CM. Addition of a neutralizing antibody to AdSparcl1 CM resulted in a decrease in tubule formation compared to hAECs cultured in AdSparcl1 CM alone. This decrease was concentration dependent with an increase in antibody concentration resulting in a decrease in tubules length. Similar observations were made in all treatment groups with the largest levels of tubule formation observed at 12 hours. By 18 hours, tubule length begins to decrease with lattice structures beginning to destabilise and degrade. The decrease in tubule length between 12 and 18 hours is lowest in the AdSparcl1 CM treatment groups suggesting a possible stabilisation effect on hAEC structure following tubule formation (FIG. 6E).

Cardioprotection

Cardiomyocytes cultured for 48 hours under hypoxic conditions were assessed for MTT and caspase activity. In all experiments, cardiomyocytes cultured under normal conditions were assumed to be 100% metabolically active. Following 48 hours hypoxia, only 47% of cardiomyocytes were mitochondrially active. Treatment of cardiomyocytes with MSC culture media did not confer any protection to cardiomyocytes during exposure to hypoxia. Additionally, following treatment with MSC CM, 51% of cardiomyocytes were metabolically active. This observation was further enhanced following treatment with AdSparcl1 transduced MSC CM as 65% of cardiomyocytes were calculated to be mitochondrially active. Addition of a Sparcl1 antibody to the AdSparcl1 MSC CM resulted in a decrease in active cardiomyocytes to MSC CM control levels (FIG. 6F).

Caspase assays quantifying caspase activity as a measure of apoptosis levels were conducted following 48 hour exposure to hypoxia. STS, a positive inducer of apoptosis was used as the positive control for this experiment. Cardiomyocytes following 48 hours of hypoxia expressed high caspase levels when compared to cardiomyocytes under normoxic conditions. Treatment of cardiomyocytes with MSC CM or AdSparcl1 transduced MSC CM conferred protection on the hypoxic cardiomyocytes with significantly decreased activity rates. Addition of Sparcl1 antibody showed an increase in caspase activity rates following its addition to AdSparcl1 transduced MSC CM (FIG. 6G).

Discussion

Despite the enormous amount of data supporting the therapeutic efficacy of MSCs in cardiac repair, controversy remains regarding the fate and function of the MSC once injected into the injured myocardium. By investigating the stem cell—host cell interaction following engraftment into the injured myocardium, we sought to better understand the complex processes of heart protection and regeneration. This study aims to elucidate the interactions of transplanted MSCs with neighbouring host tissue and explore subsequent alterations to MSC phenotype and genotype.

Determining the phenotype and molecular footprint of the engrafted MSC will aide our understanding of the therapeutic action of these cells and provide enhanced opportunities for exploiting their beneficial effects. Following the retrieval of transplanted (IMC delivered) MSCs in vivo microarray analysis was performed, thereby identifying a number of differentially regulated genes with potential therapeutically relevant functions in the setting of cardiovascular disease. Similar trends in gene expression were observed by RT-PCR validating changes in gene expression as determined by microarray. Microarray analysis of retrieved samples identified a number of dysregulated genes associated with angiogenesis, cytoprotection, migration and immuno-modulation, all of which are of great clinical relevance in cardiac repair. Identifying specifically secreted paracrine factors released by MSCs provides a novel and exciting avenue to better understand the therapeutic mechanism of these cells in vivo. Determining the functional effect of these genes in cardiovascular repair and regeneration provides an avenue through which the therapeutic efficacy of these cells can be harnessed. Utilising these data to genetically modify or precondition MSCs prior to transplantation will provide an avenue for improving functional outcome and enhancing the modest natural reparative effects reported with unmodified MSCs.

Despite major advances in our understanding and treatment of coronary artery disease, MI is still responsible for a significant proportion of morbidity and mortality worldwide. The underlying cause of its pathophysiology stems from the death of cardiomyocytes due to the ischemic environment and a lack of blood supply following occlusion of the LAD.

The endogenous reparative capacity of the heart seems unable to regenerate significant quantities of tissue leading to chronic ischemic cardiomyopathy and congestive heart failure (Beltrami, et al 2001). The development of MSCs as a cellular therapeutic for post-MI patients is underway and the feasibility and safety of MSCs has been established in a number of clinical trials (Katritsis, et al 2005, Strauer, et al 2002).

Through the investigation of the gene expression profiles of transplanted MSCs retrieved from the ischemic MI environment after 1 week, we sought to uncover the molecular footprint of the engrafted cell. Through microarray functional cluster analysis, several potential therapeutic targets were identified. Particular attention was paid to genes encoding secreted proteins found to be upregulated in the retrieved MSC population. The most highly upregulated gene Sfrp2 has recently been described by Mirotsou et al to exert multiple biological effects including cardioprotection both in vitro and in vivo (Mirotsou, et al 2007). The next most highly upregulated gene Sparcl1, an extracellular matrix (ECM) molecule has become the focus of our research efforts. The cardiac interstitium is a unique and adaptable ECM that provides an environment in which myocytes, fibroblasts, and endothelial cells communicate and function (McCurdy, et al 2009). Sparcl1 is a member of the SPARC family of proteins, which have previously been described to prevent cardiac dilation and dysfunction following MI (Schellings, et al 2009). However, the role of Sparcl1 has not been described in cardiac repair or been associated with MSC therapy.

To determine if hypoxia alone in the infarct environment was responsible for differences in gene expression observed in the retrieved MSC population compared to control, the expression of several genes was investigated following MSC exposure to hypoxia. When compared to control, the expression of many of the genes investigated remained the same. Two genes, TEK and Angptl4 demonstrated increased expression as a result of exposure to hypoxia. These data suggest that the effect of hypoxia alone is not sufficient to induce expression of these genes but that inflammation and other factors may be involved. RT-PCR analysis of the same gene set was performed in both healthy and infarcted myocardial tissue. The expression of two genes, Sfrp2 and Angptl4 were significantly increased in infarcted cardiac tissue compared to healthy heart controls. Together these data suggest that the large increase in Sparcl1 expression observed following microarray analysis was not attributable to hypoxia exposure alone but may be the result of their interactions with resident cardiomyocytes in the damaged heart.

Angiogenesis is an essential process involved in myocardial tissue repair. The importance of restoring a vascular supply to injured myocardium is of critical importance. MSCs have been shown in vitro to release a number of pro-angiogenic cytokines during culture including VEGF, PDGF and Angptl1 (Kinnaird, et al 2004). This finding is supported by in vivo reports of increased vascular density and reperfusion following MSC administration in pre-clinical models of MI (Kamihata, et al 2001, Tang, et al 2005). Here, retrieved MSCs have increased expression of a number of genes involved in angiogenesis. Two of the most highly transcribed genes, TEK and Angptl4 were investigated for their role in tubule formation and angiogenesis. Sparcl1, implicated in tumour progression and vascularisation (Barker, et al 2005, Lau, et al 2006); has not been previously demonstrated to influence vessel formation and structure in the setting of MI. Following recombinant protein treatment of hAECs, an increase in tubule formation and vascular density was observed in all treatment groups. Angptl4, a secreted protein belonging to the angiopoietin family, resulted in a 5-fold increase in tubule length when compared to control. TEK, also known as Tie 2, resulted in a 4-fold increase in tubule length. Addition of Sparcl1 recombinant protein resulted in a 3-fold increase in tubule length when compared to control. The release of pro-angiogenic factors by MSCs following engraftment supports previously published data describing MSCs as inducers of neovascularisation (Kamihata, et al 2001) and indicates the therapeutic potential of MSCs as pro angiogenic mediators in cardiac repair.

Stimulating the migration of cell types necessary to rebuild the damaged myocardium following MI is essential for the remodelling process. Here, the stimulatory effect of Sparcl1 recombinant protein on the migration of two predominant cell types, hAECs and SMCs that reside in the myocardium and have important functional roles in the creation of new blood vessels and neovascularisation was investigated. Sparcl1 did not stimulate the migration of either cell type although insignificant levels of migrating cells were observed in both cases. Sparcl1 did however stimulate the migration of MSCs indicating a possible role in the retention of MSCs in the ischemic myocardium.

Sparcl1 expression by MSCs engrafted within the infarcted myocardium was confirmed by immunofluorescence and high powered confocal imaging. Although Sparcl1 expression was observed throughout the myocardium, its expression was significantly increased in and adjacent to the MSC injection tract. Confocal imaging of PKH-26 MSCs in the injection tract demonstrated co-localisation of Sparcl1 expression with MSCs indicating that Sparcl1 was being secreted by the engrafted cells. As demonstrated in vitro, hypoxia alone was not responsible for the increase in expression of Sparcl1 by MSCs, however following exposure of MSCs to cardiomyocyte CM, a significant increase in Sparcl1 expression was observed. Increased expression was further enhanced by exposure of hypoxic MSCs to CM from hypoxic cardiomyocytes indicating a clear interplay between MSCs and cardiomyocytes in MSC expression of Sparcl1.

The underlying cause of acute MI is the damage and loss of viable cardiomyocytes in the injured myocardium. Stem cell cardiomyoplasty aims to modify this basic pathophysiology after an MI. Conferring protection to these resident cardiomyocytes could prove an effective way in reducing cell death and therefore, the detrimental downstream effects associated with cardiomyocyte death. MSC-treated hearts display a decrease in the pro-apoptotic gene Bax (Tang, et al 2005) suggesting a protective role by transplanted MSCs. In this study, cytoprotective factors were identified that may potentially be involved in the protection of cardiomyocytes following MI. Using an in vitro model of hypoxia, the effects of Sparcl1 recombinant protein were assessed on hypoxia damaged cardiomyocytes. Sparcl1 treatment during hypoxia resulted in a dramatic increase in cell viability when compared to cardiomyocytes in hypoxia alone. A decrease in caspase activity was also observed indicating a reduction in cell apoptosis following Sparcl1 treatment of cardiomyocytes. Similar observations were made for Sfrp2 treated cardiomyocytes confirming a role for both proteins in cardiomyocyte protection during hypoxia. Up regulation of both of these genes in retrieved MSCs provides convincing evidence for the role of MSCs in cytoprotection, an effect that could potentially be augmented through the genetic modification of these cells. The role of Sparcl1 has not yet been reported in the context of MI and is a novel therapeutic candidate for cardiac repair. Sparcl1 is upregulated by MSCs when they are exposed to hypoxically injured cardiomyocytes, suggesting that Sparcl1 is part of the injury response that MSCs exhibit. Sparcl1 also helps tubule formation in a way that suggests that it is a proangiogenic mediator.

MSCs secrete a number of therapeutically relevant factors involved in the suppression of the immune system, fibrosis and apoptosis inhibition and enhanced angiogenesis (Caplan and Dennis 2006). Harnessing this inherent reparative potential of MSCs and supplementing it with genetic modification provides researchers with an avenue to improve the apparent beneficial effects of MSC therapy. Through over-expression of Sparcl1 by adenoviral transduction, we have established a stably expressing cell for use in both in vitro and in vivo functional experiments. By harvesting CM from these cells confirmed to express large quantities of Sparcl1, we investigated the paracrine effects of AdSparcl1 MSCs on angiogenesis and cardioprotection. Unmodified MSC CM promoted tubule formation, confirming previous data, reporting the pro-angiogenic effects of MSCs. The angiogenic effect was enhanced in AdSparcl1 transduced MSC CM groups. Treatment of hAECS with AdSparcl1 transduced MSC CM resulted in a significant increase in tubule formation and cell sprouting compared to control. Addition of a neutralizing antibody against Sparcl1 to CM resulted in a decrease in tubule formation indicating a direct role for Sparcl1 in tubule formation and vasculogenesis. This in vitro paracrine effect holds great promise for the enhancement of in vivo neo-vascularisation following administration of these genetically modified MSCs to the damaged myocardium.

Genetic modification of MSCs has been previously carried out by many research groups in the past reporting that over-expression of pro-survival genes in MSCs increases the levels of cell engraftment, cell survival and functional improvement following administration (Li, et al 2007, Song, et al 2005). The paracrine effect of Adsparcl1 transduced MSCs was assessed in cardioprotection assays using CM from these cells. Following treatment of cardiomyocytes with AdSparcl1 transduced MSC CM during hypoxia, a decrease in caspase activity was observed together with an increase in mitochondrial activity, an indicator of cell viability. Despite the modest cardioprotective effect observed following treatment with control MSC CM, the cytoprotective effect was further enhanced following treatment with AdSparcl1 CM. Genetic manipulation of MSCs is a promising therapeutic strategy for the successful treatment of cardiovascular disease by enhancing their inherent reparative capacity.

Studies that show stem cells express and release biologically active mediators have important implications in the understanding of basic stem cell biology and their clinical mechanism of action. A comprehensive characterisation of MSC therapeutic paracrine factors and their pathways will allow for the identification of possible novel therapeutic targets and/or pharmaceutical agents. Furthermore, it provides a therapeutic avenue for stem cells to become gene delivery vehicles whose secreted gene products can exert enhanced paracrine and possibly autocrine effects in future therapeutic approaches. Genetic modification approaches further increase the reparative potential of MSCs through increasing not only stem cell and cardiomyocyte survival in the harsh hypoxic environment but also enhance production of powerful cytoprotective paracrine factors. Gene therapy and stem cell therapy combinations show huge promise as cardiovascular disease therapeutics and will enhance potential stem cell cardiomyoplasty in the future.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

Asahara, T., Masuda, H., Takahashi, T., Kalka, C., Pastore, C., Silver, M., Kearne, M., Magner, M. & Isner, J. M. (1999) Bone marrow origin of endothelial progenitor cells responsible for postnatal vasculogenesis in physiological and pathological neovascularization. *Circ Res*, 85, 221-228.

Barker, T. H., Framson, P., Puolakkainen, P. A., Reed, M., Funk, S. E. & Sage, E. H. (2005) Matricellular homologs in the foreign body response: hevin suppresses inflammation, but hevin and SPARC together diminish angiogenesis. *Am J Pathol*, 166, 923-933.

Beltrami, A. P., Urbanek, K., Kajstura, J., Yan, S. M., Finato, N., Bussani, R., Nadal-Ginard, B., Silvestri, F., Leri, A., Beltrami, C. A. & Anversa, P. (2001) Evidence that human cardiac myocytes divide after myocardial infarction. *N Engl J Med*, 344, 1750-1757.

Caplan, A. I. & Dennis, J. E. (2006) Mesenchymal stem cells as trophic mediators. *J Cell Biochem*, 98, 1076-1084.

Dobson, K. R., Reading, L., haberey, M., Marine, X. & Scutt, A. (1999) Centrifugal isolation of bone marrow from bone: an improved method for the recovery and quantitation of bone marrow osteoprogenitor cells from rat tibiae and femurae.

Gnecchi, M., He, H., Noiseux, N., Liang, O. D., Zhang, L., Morello, F., Mu, H., Melo, L. G., Pratt, R. E., Ingwall, J. S. & Dzau, V. J. (2006) Evidence supporting paracrine hypothesis for Akt-modified mesenchymal stem cell-mediated cardiac protection and functional improvement. *Faseb J*, 20, 661-669.

Halkos, M. E., Zhao, Z. Q., Kerendi, F., Wang, N. P., Jiang, R., Schmarkey, L. S., Martin, B. J., Quyyumi, A. A., Few, W. L., Kin, H., Guyton, R. A. & Vinten-Johansen, J. (2008) Intravenous infusion of mesenchymal stem cells enhances regional perfusion and improves ventricular function in a porcine model of myocardial infarction. *Basic Res Cardiol*, 103, 525-536.

Kamihata, H., Matsubara, H., Nishiue, T., Fujiyama, S., Tsutsumi, Y., Ozono, R., Masaki, H., Mori, Y., Iba, O., Tateishi, E., Kosaki, A., Shintani, S., Murohara, T., Imaizumi, T. & Iwasaka, T. (2001) Implantation of bone marrow mononuclear cells into ischemic myocardium enhances collateral perfusion and regional function via side supply of angioblasts, angiogenic ligands, and cytokines. *Circulation*, 104, 1046-1052.

Katritsis, D. G., Sotiropoulou, P. A., Karvouni, E., Karabinos, I., Korovesis, S., Perez, S. A., Voridis, E. M. & Papamichail, M. (2005) Transcoronary transplantation of autologous mesenchymal stem cells and endothelial progenitors into infarcted human myocardium. *Catheter Cardiovasc Interv*, 65, 321-329.

Kinnaird, T., Stabile, E., Burnett, M. S., Shou, M., Lee, C. W., Barr, S., Fuchs, S. & Epstein, S. E. (2004) Local delivery of marrow-derived stromal cells augments collateral perfusion through paracrine mechanisms. *Circulation*, 109, 1543-1549.

Lau, C. P., Poon, R. T., Cheung, S. T., Yu, W. C. & Fan, S. T. (2006) SPARC and Hevin expression correlate with tumour angiogenesis in hepatocellular carcinoma. *J Pathol*, 210, 459-468.

Le Jan, S., Amy, C., Cazes, A., Monnot, C., Lamande, N., Favier, J., Philippe, J., Sibony, M., Gasc, J. M., Corvol, P. & Germain, S. (2003) Angiopoietin-like 4 is a proangiogenic factor produced during ischemia and in conventional renal cell carcinoma. *Am J Pathol*, 162, 1521-1528

Li, W., Ma, N., Ong, L. L., Nesselmann, C., Klopsch, C., Ladilov, Y., Furlani, D., Piechaczek, C., Moebius, J. M., Lutzow, K., Lendlein, A., Stamm, C., Li, R. K. & Steinhoff, G. (2007) Bcl-2 engineered MSCs inhibited apoptosis and improved heart function. *Stem Cells*, 25, 2118-2127.

Liu, Z., Zhang, Z., Ma, J., Zhang, M., Luo, L., Xiao, Q., Lin, J., Zhang, P. & Chen, J. (2002) An experimental study of anti-angiogenesis with recombinant human kringle 5. *Zhonghua Yan Ke Za Zhi*, 38, 415-418.

McCurdy, S., Baicu, C. F., Heymans, S. & Bradshaw, A. D. (2009) Cardiac extracellular matrix remodeling: Fibrillar collagens and Secreted Protein Acidic and Rich in Cysteine (SPARC). *J Mol Cell Cardiol*.

Mirotsou, M., Zhang, Z., Deb, A., Zhang, L., Gnecchi, M., Noiseux, N., Mu, H., Pachori, A. & Dzau, V. (2007) Secreted frizzled related protein 2 (Sfrp2) is the key Akt-mesenchymal stem cell-released paracrine factor mediating myocardial survival and repair. *Proc Natl Acad Sci USA*, 104, 1643-1648.

Schellings, M. W., Vanhoutte, D., Swinnen, M., Cleutjens, J. P., Debets, J., van Leeuwen, R. E., d'Hooge, J., Van de Werf, F., Carmeliet, P., Pinto, Y. M., Sage, E. H. & Heymans, S. (2009) Absence of SPARC results in increased cardiac rupture and dysfunction after acute myocardial infarction. *J Exp Med*, 206, 113-123.

Simpson, P., McGrath, A. & Savion, S. (1982) Myocyte hypertrophy in neonatal rat heart cultures and its regulation by serum and by catecholamines. *Circ Res*, 51, 787-801.

Slevin, M., Krupinski, J., Rovira, N., Turu, M., Luque, A., Baldellou, M., Sanfeliu, C., de Vera, N. & Badimon, L. (2009) Identification of pro-angiogenic markers in blood vessels from stroked-affected brain tissue using laser-capture microdissection. *BMC Genomics*, 10, 113.

Song, H., Kwon, K., Lim, S., Kang, S. M., Ko, Y. G., Xu, Z., Chung, J. H., Kim, B. S., Lee, H., Joung, B., Park, S., Choi, D., Jang, Y., Chung, N. S., Yoo, K. J. & Hwang, K. C. (2005) Transfection of mesenchymal stem cells with the FGF-2 gene improves their survival under hypoxic conditions. *Mol Cells*, 19, 402-407.

Strauer, B. E., Brehm, M., Zeus, T., Kostering, M., Hernandez, A., Sorg, R. V., Kogler, G. & Wernet, P. (2002) Repair of infarcted myocardium by autologous intracoronary mononuclear bone marrow cell transplantation in humans. *Circulation*, 106, 1913-1918.

Tang, Y. L., Zhao, Q., Qin, X., Shen, L., Cheng, L., Ge, J. & Phillips, M. I. (2005) Paracrine action enhances the effects of autologous mesenchymal stem cell transplantation on vascular regeneration in rat model of myocardial infarction. *Ann Thorac Surg*, 80, 229-236; discussion 236-227.

Tressel, S. L., Kim, H., Ni, C. W., Chang, K., Velasquez-Castano, J. C., Taylor, W. R., Yoon, Y. S. & Jo, H. (2008) Angiopoietin-2 stimulates blood flow recovery after femoral artery occlusion by inducing inflammation and arteriogenesis. *Arterioscler Thromb Vasc Biol*, 28, 1989-1995.

Wollert, K. C. & Drexler, H. (2005) Clinical applications of stem cells for the heart. *Circ Res*, 96, 151-163.

The invention claimed is:

1. A pharmaceutical composition comprising cells, wherein the cells comprise a vector encoding Sparcl1, wherein the cells are mesenchymal stem cells, endothelial progenitor cells, induced pluripotent stem cells, or combinations thereof.

2. A method of treating a vascular disease, a vascular complication, an orthopedic condition, or a degenerative joint disease, in a patient, the method comprising the step of administering to the patient a pharmaceutical composition comprising Sparcl1 in an amount effective to treat a vascular disease, a vascular complication, an orthopedic condition, or a degenerative joint disease.

3. A method of treating a vascular disease, a vascular complication, an orthopedic condition, or a degenerative joint disease, in a patient, the method comprising the step of administering to the patient a pharmaceutically effective amount of a polynucleotide wherein sequence of the polynucleotide encodes Sparcl1, wherein Sparcl1 is expressed in an amount effective to treat a vascular disease, a vascular complication, an orthopedic condition, or a degenerative joint disease.

4. A method of treating a vascular disease or a vascular complication, orthopedic conditions, degenerative joint disease, or effecting wound healing and repair, the method comprising the step of administering to a patient mesenchymal stem cells which express or overexpress Sparcl1.

5. The method as claimed in any of claims 3 to 4, wherein the vascular disease or a vascular complication is myocardial infarction, peripheral vascular disease, ischemia, cerebrovascular disease, diabetes mellitus, dyslipidaemia, hypertension, or a combination thereof.

6. A medical device coated with (a) Sparcl1, (b) a vector encoding Sparcl1, (c) mesenchymal stem cells expressing or overexpressing Sparcl1, or (d) a combination thereof, wherein the medical device is a stent, a suture, a dressing, a prosthesis, or combinations thereof.

7. The pharmaceutical composition of claim 1, wherein the vector is an adenoviral vector.

* * * * *